(12) United States Patent
Samproni et al.

(10) Patent No.: US 12,326,442 B2
(45) Date of Patent: Jun. 10, 2025

(54) DEVICE WITH A FLUID COMPONENT ASSESSMENT FEATURE

(71) Applicant: Siemens Healthcare Diagnostics Inc., Tarrytown, NY (US)

(72) Inventors: Jennifer Samproni, Braintree, MA (US); Manish Deshpande, Newton, MA (US); Peter Paulicka, Röttenbach (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 637 days.

(21) Appl. No.: 17/299,821

(22) PCT Filed: Dec. 5, 2019

(86) PCT No.: PCT/US2019/064627
§ 371 (c)(1),
(2) Date: Jun. 4, 2021

(87) PCT Pub. No.: WO2020/118021
PCT Pub. Date: Jun. 11, 2020

(65) Prior Publication Data
US 2022/0023857 A1   Jan. 27, 2022

Related U.S. Application Data

(60) Provisional application No. 62/776,825, filed on Dec. 7, 2018.

(51) Int. Cl.
*G01N 33/49* (2006.01)
*B01L 3/00* (2006.01)
(Continued)

(52) U.S. Cl.
CPC ............ *G01N 33/491* (2013.01); *B01L 3/508* (2013.01); *G01N 21/251* (2013.01); *G01N 21/77* (2013.01);
(Continued)

(58) Field of Classification Search
CPC .. G01N 1/4077; G01N 29/222; G01N 33/491; G01N 21/251; G01N 21/77;
(Continued)

(56) References Cited

U.S. PATENT DOCUMENTS

| 3,954,623 A | 5/1976 | Hammer et al. |
| 4,844,871 A * | 7/1989 | Polaschegg ........ A61B 5/14539 |
| | | 210/651 |

(Continued)

FOREIGN PATENT DOCUMENTS

| CN | 2240724 Y | 11/1996 |
| EP | 0597268 A1 | 5/1994 |

(Continued)

OTHER PUBLICATIONS

European Search Report and Search Opinion of European Patent Application No. 19893029.9 dated Jan. 5, 2022.

(Continued)

*Primary Examiner* — Michael P LaPage
*Assistant Examiner* — Roberto Fabian, Jr.

(57) ABSTRACT

A device including a housing, a zone and a means for testing a fluid sample within the housing is disclosed. The housing is constructed of a fluid impermeable material, and defines a first fluid port, and a second fluid port. The first fluid port is configured to connect to a fluid collection device to receive a fluid sample from the fluid collection device into the housing. The second port is configured to pass the fluid sample from the housing into a testing instrument. The zone is formed in the housing. The zone is constructed of a (Continued)

material that allows an analysis of the fluid sample positioned within the housing, and located adjacent to the zone.

17 Claims, 16 Drawing Sheets

(51) Int. Cl.
*G01N 21/25* (2006.01)
*G01N 21/77* (2006.01)

(52) U.S. Cl.
CPC ..... *G01N 33/4915* (2013.01); *G01N 33/4925* (2013.01); *B01L 2200/0689* (2013.01); *B01L 2200/16* (2013.01); *B01L 2300/0663* (2013.01); *B01L 2300/0681* (2013.01); *B01L 2400/0478* (2013.01); *G01N 2021/7763* (2013.01); *G01N 2201/0221* (2013.01)

(58) Field of Classification Search
CPC .......... G01N 33/4915; G01N 33/4925; G01N 2021/7763; G01N 2201/0221; A61B 5/150755; A61B 5/150221; A61B 5/150351; A61B 5/150969; A61B 5/150435; A61B 5/157; A61B 5/15003; A61B 5/150786; A61B 5/150793; B01L 2300/0681; B01L 3/502; B01L 2200/10; B01L 2300/042; B01L 2200/16; A61M 1/34; A61M 1/3403; B01D 63/087; B01D 69/088

See application file for complete search history.

(56) References Cited

U.S. PATENT DOCUMENTS

| | | |
|---|---|---|
| 5,125,415 A | 6/1992 | Bell |
| 5,330,420 A | 7/1994 | Lee |
| 5,876,605 A | 3/1999 | Kitajima et al. |
| 5,979,669 A | 11/1999 | Kitajima et al. |
| 5,996,811 A | 12/1999 | Kitajima et al. |
| 6,045,699 A | 4/2000 | Yazawa et al. |
| 6,196,998 B1 | 3/2001 | Jansen et al. |
| 6,217,540 B1 | 4/2001 | Kitajima et al. |
| 6,220,453 B1 | 4/2001 | Kitajima et al. |
| 6,225,130 B1 | 5/2001 | Kitajima et al. |
| 6,280,621 B1 | 8/2001 | Yazawa et al. |
| 6,328,167 B1 | 12/2001 | Seshimoto et al. |
| 6,375,856 B1 | 4/2002 | Seshimoto et al. |
| 6,383,818 B1 | 5/2002 | Arai et al. |
| 6,387,290 B1 | 5/2002 | Brody et al. |
| 6,405,876 B1 | 6/2002 | Seshimoto et al. |
| 6,659,288 B2 | 12/2003 | Amano et al. |
| 6,659,975 B2 | 12/2003 | Amano et al. |
| 6,936,473 B2 | 8/2005 | Nanba et al. |
| RE39,457 E * | 1/2007 | Guirguis .......... G01N 33/54366 436/514 |
| 7,323,144 B2 | 1/2008 | Arai et al. |
| 7,407,578 B2 | 8/2008 | Sakaino et al. |
| 7,500,569 B2 | 3/2009 | Manoussakis et al. |
| 7,896,818 B2 | 3/2011 | Fremming et al. |
| 7,927,810 B2 | 4/2011 | Togawa et al. |
| 8,057,672 B2 | 11/2011 | Chung et al. |
| 8,444,621 B2 | 5/2013 | Fremming et al. |
| 8,535,617 B2 | 9/2013 | MacDonald et al. |
| 8,574,497 B2 | 11/2013 | Pfaff |
| 8,846,333 B2 | 9/2014 | Karlsson |
| 8,865,003 B2 | 10/2014 | Yang |
| 8,999,268 B2 | 4/2015 | Egger-Cimenti et al. |
| 9,028,688 B2 | 5/2015 | Okamoto et al. |
| 9,261,494 B2 | 2/2016 | Choi et al. |
| 9,283,313 B2 | 3/2016 | Huemer |
| 9,322,761 B2 | 4/2016 | Miller |
| 9,427,707 B2 | 8/2016 | Montagu et al. |
| 9,517,026 B2 | 12/2016 | Gelfand et al. |
| 9,597,028 B2 | 3/2017 | Marchiarullo |
| 9,757,095 B2 | 9/2017 | Terbrueggen et al. |
| 9,816,979 B2 | 11/2017 | Kelso et al. |
| 9,983,199 B2 | 5/2018 | Karlsson |
| 9,993,816 B2 | 6/2018 | Biesbrouck |
| 10,111,610 B2 | 10/2018 | Tan et al. |
| 2001/0039057 A1* | 11/2001 | Douglas .......... G01N 33/54366 422/417 |
| 2002/0036170 A1 | 3/2002 | Harvey et al. |
| 2003/0185707 A1 | 10/2003 | Iwaki et al. |
| 2004/0035792 A1 | 2/2004 | Rauch et al. |
| 2005/0227370 A1 | 10/2005 | Ramel et al. |
| 2006/0016747 A1 | 1/2006 | Sakaino et al. |
| 2008/0003141 A1 | 1/2008 | Iketani |
| 2008/0017577 A1 | 1/2008 | Yi et al. |
| 2010/0111763 A1 | 5/2010 | Kahn et al. |
| 2011/0076697 A1 | 3/2011 | Ruvinsky et al. |
| 2012/0086938 A1 | 4/2012 | Folkenberg |
| 2012/0232803 A1 | 9/2012 | Viola et al. |
| 2013/0040333 A1 | 2/2013 | Karlsson |
| 2013/0184188 A1 | 7/2013 | Ewart et al. |
| 2014/0305196 A1 | 10/2014 | Ellis et al. |
| 2014/0308165 A1* | 10/2014 | Marchiarullo ... A61B 5/150213 422/534 |
| 2014/0329268 A1 | 11/2014 | Karlsson |
| 2015/0090674 A1 | 4/2015 | Lee et al. |
| 2015/0153323 A1 | 6/2015 | Huemer |
| 2016/0074569 A1 | 3/2016 | Schuetz et al. |
| 2016/0096148 A1 | 4/2016 | Schuetz et al. |
| 2016/0106353 A1 | 4/2016 | Schuetz et al. |
| 2016/0106907 A1 | 4/2016 | Winkler et al. |
| 2016/0202237 A1 | 7/2016 | Zeng et al. |
| 2016/0258937 A1 | 9/2016 | Ellington et al. |
| 2016/0258945 A1 | 9/2016 | Malima et al. |
| 2016/0313298 A1 | 10/2016 | Wright et al. |
| 2017/0059550 A1 | 3/2017 | Bokka Srinivasa Rao et al. |
| 2017/0095190 A1 | 4/2017 | Sloan et al. |
| 2017/0108516 A1 | 4/2017 | Ledden et al. |
| 2017/0241977 A1 | 8/2017 | Wilson et al. |
| 2017/0248618 A1 | 8/2017 | Baxter et al. |
| 2017/0252706 A1* | 9/2017 | Xu .......... B01D 71/50 |
| 2017/0299481 A1 | 10/2017 | Laugham, Jr. |
| 2017/0328896 A1* | 11/2017 | Luloh .......... G01N 33/558 |
| 2017/0354362 A1 | 12/2017 | Xu et al. |
| 2018/0125464 A1 | 5/2018 | Kolb et al. |
| 2018/0128807 A1 | 5/2018 | Ishizaka et al. |
| 2018/0128844 A1 | 5/2018 | Ishizaka et al. |
| 2018/0136194 A1 | 5/2018 | Sinn Blandy et al. |
| 2018/0143116 A1 | 5/2018 | Urano et al. |
| 2018/0230508 A1 | 8/2018 | Idelevich et al. |
| 2018/0304261 A1 | 10/2018 | Ho et al. |
| 2018/0321228 A1 | 11/2018 | Cooper et al. |
| 2019/0046715 A1 | 2/2019 | Margraf et al. |
| 2019/0072539 A1 | 3/2019 | Eriksson et al. |

FOREIGN PATENT DOCUMENTS

| | | | |
|---|---|---|---|
| JP | 2015503104 A | 1/2015 | |
| JP | 2015530566 A | 10/2015 | |
| WO | 2007000986 A1 | 1/2007 | |
| WO | 2009110089 A1 | 9/2009 | |
| WO | 2010113355 A1 | 7/2010 | |
| WO | 2014019254 A1 | 2/2014 | |
| WO | 2014172234 A1 | 10/2014 | |
| WO | 2014207140 A1 | 12/2014 | |
| WO | 2014207150 A1 | 12/2014 | |
| WO | WO-2015191450 A1 * | 12/2015 | .......... G01N 33/558 |
| WO | WO-2018065626 A1 * | 4/2018 | ........ B01L 3/502761 |
| WO | 2018226994 A1 | 12/2018 | |
| WO | 2019025914 A1 | 2/2019 | |
| WO | 2020118018 A1 | 6/2020 | |

(56) References Cited

FOREIGN PATENT DOCUMENTS

| WO | 2020185272 A1 | 9/2020 |
| WO | 2021015808 A1 | 1/2021 |

OTHER PUBLICATIONS

International Search Report and Written Opinion of International Application No. PCT/US2019/064627 dated Feb. 25, 2020.
Liu et al., "Membrane-based, sedimentation-assisted plasma separator for point-of-care applications", Nov. 5, 2013, Anal Chem. 85(21), pp. 1-17.
Adiga et al., "Hemolytic index—A tool to measure hemolysis in vitro", 2016, IOSR Journal of Biotechnology and Biochemistry, vol. 2, Issue 2, pp. 49-52.
McCaughey et al., "Current Methods of Haemolysis Detection and Reporting as a Source of Risk to Patient Safety: a Narrative Review", 2016, Clin Biochem Rev 37 (4), pp. 143-151.
Peter J. Howanitz MD, Presentation on Hemolysis, <https://www.slideserve.com/altessa/peter-j-howanitz-md>, Jul. 20, 2014, pp. 1-30.
Zhou et al., "Optofluidic Sensor for Inline Hemolysis Detection on Whole Blood", Feb. 2018, ACS Sensors, 3, pp. 784-791.

\* cited by examiner

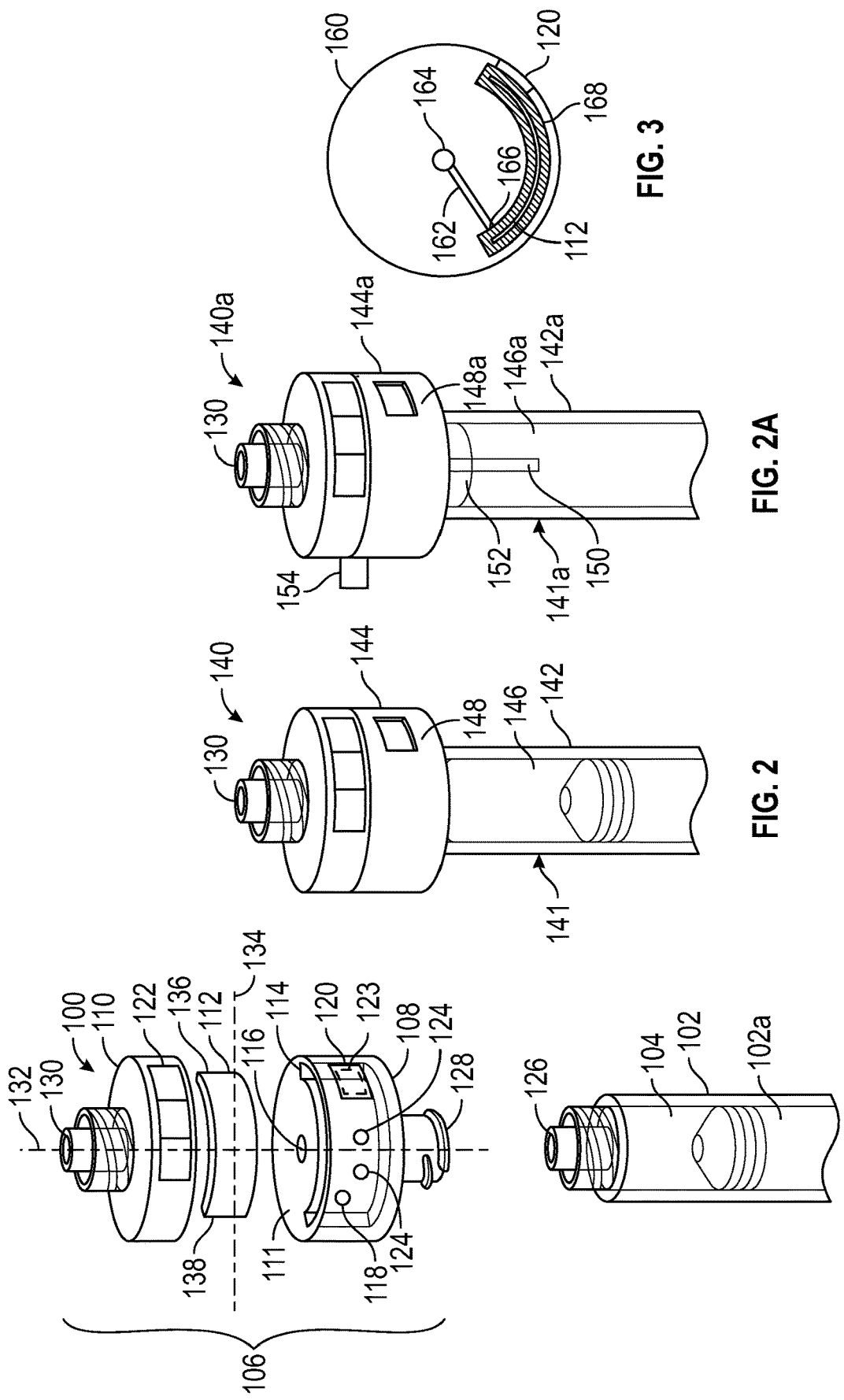

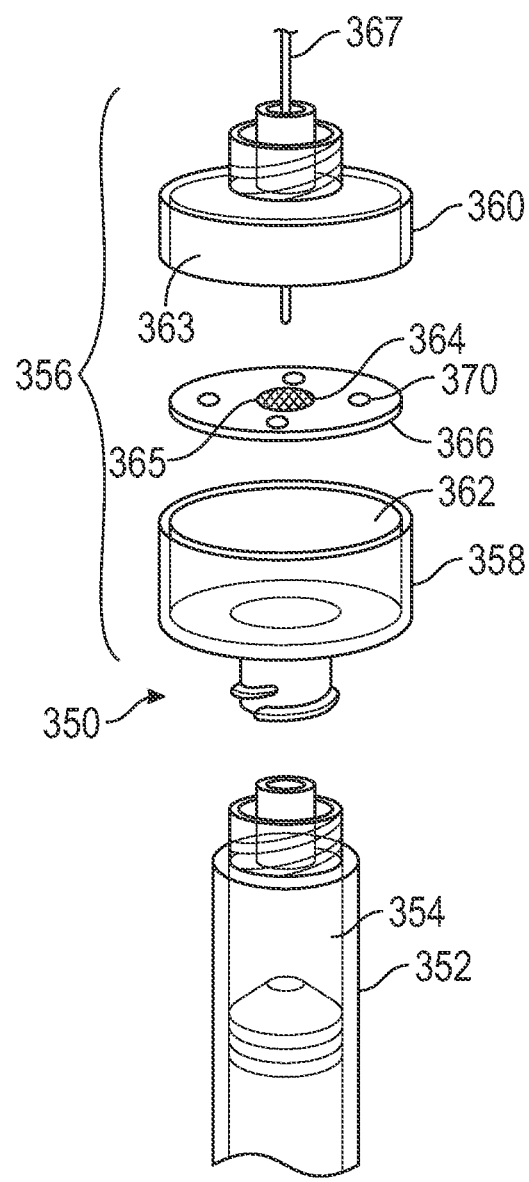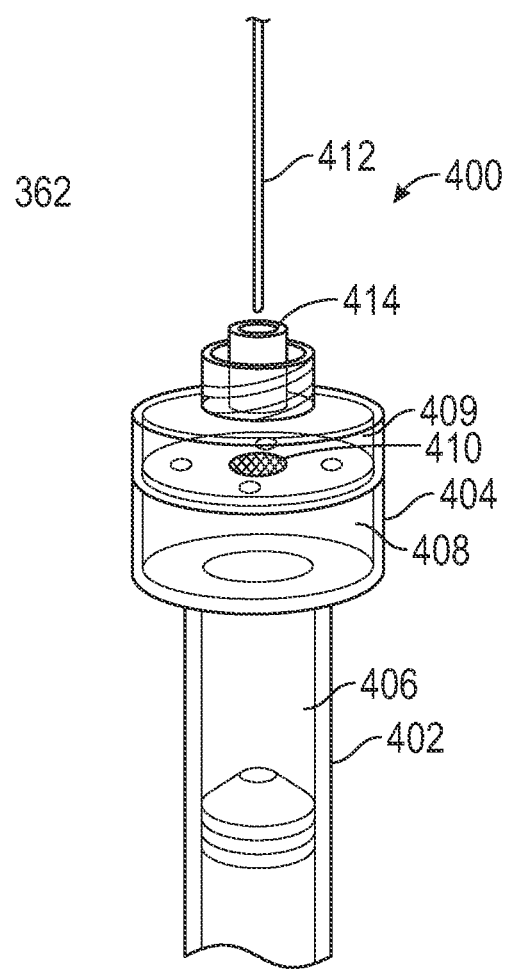
FIG. 10
FIG. 11

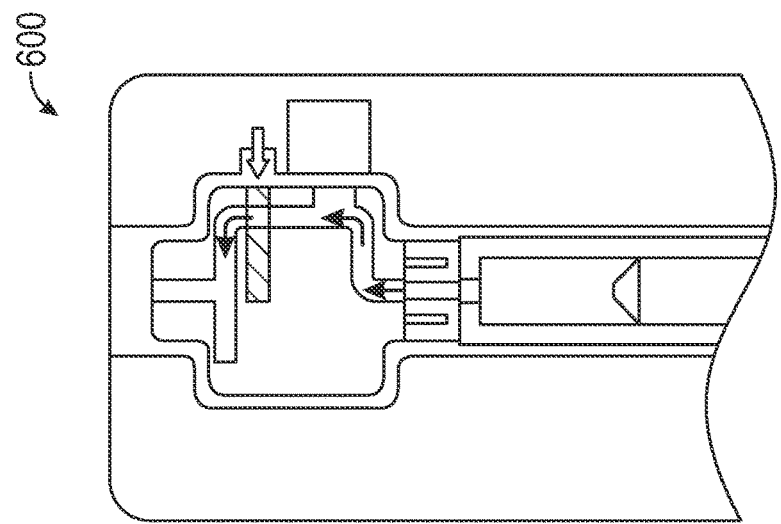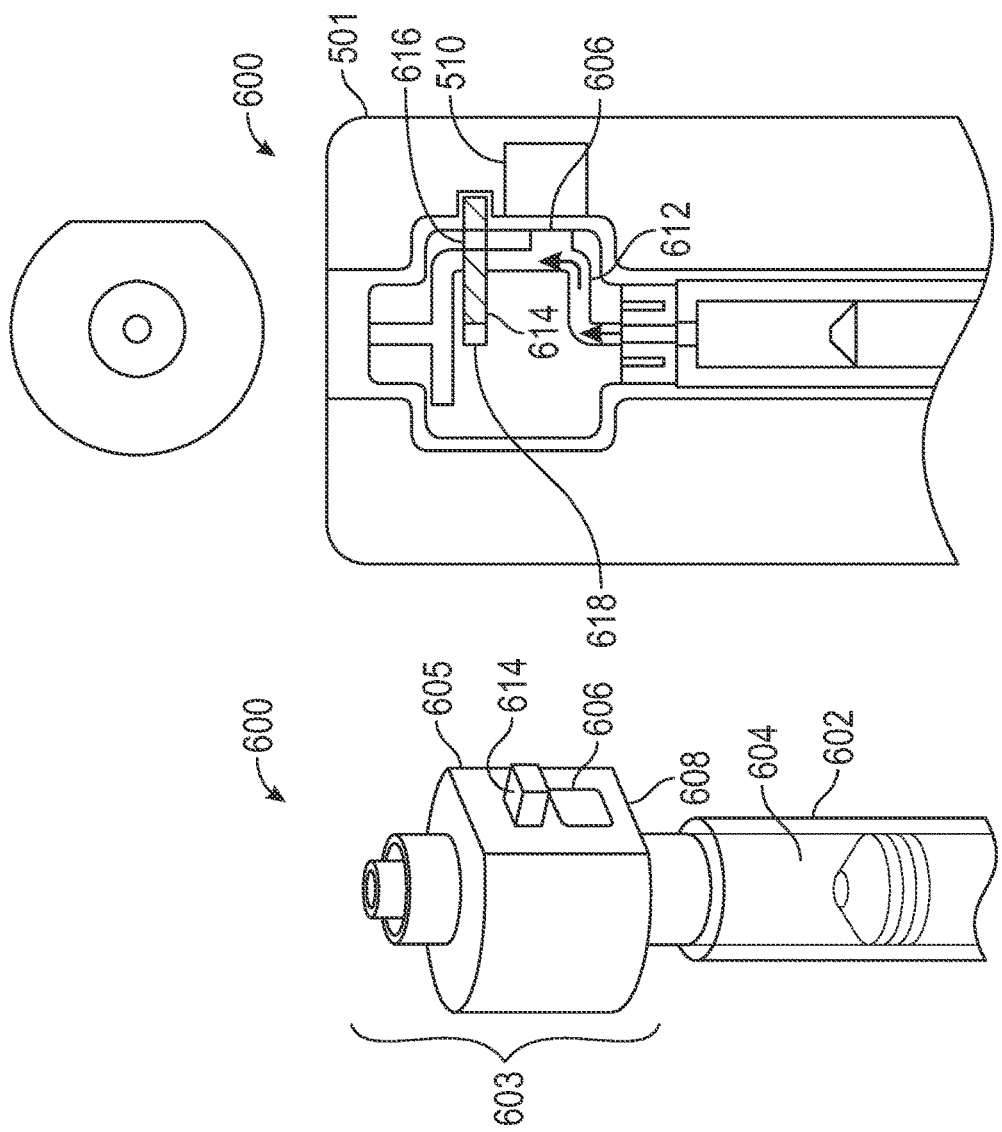

DEVICE WITH A FLUID COMPONENT ASSESSMENT FEATURE

CROSS REFERENCE TO RELATED APPLICATIONS

This application claims the benefit of U.S. Provisional Application No. 62/776,825 filed Dec. 7, 2018, the entirety of which is hereby incorporated by reference.

STATEMENT REGARDING FEDERALLY SPONSORED RESEARCH AND DEVELOPMENT

Not Applicable.

BACKGROUND

Point-of-care testing refers generally to medical testing at or near the site of patient care, such as in an emergency room. A desired outcome of such tests is often rapid and accurate lab results to determine a next course of action in the patient care. A number of such point of care tests involve analysis of a blood sample from the patient. Prior to testing the sample, it may be necessary or beneficial to treat the sample by for instance separating a whole blood sample into components, adding a reagent, or removing a component. In some cases, pure plasma is separated from the source whole blood sample. However, even in such plasma samples, there are often residual broken blood cells as a result of hemolysis due to imperfections in obtaining the sample from the subject, pre-analytical blood sample handling, and the whole blood separation process. Hemolyzed cells can interfere with the integrity of analytical test results, whether in whole blood or plasma.

For example, if hemolysis occurs, resulting free hemoglobin in the sample may cause interference in a number of tests, thereby leading to a signal reduction, reduced measurement accuracy and precision, or to false positive results at the other end of the spectrum. For one, it has been found that the potassium concentration in a corresponding sample with lysis of red blood cells may increase significantly and cause a high risk of misdiagnosis in a diagnostic test for potassium levels.

To determine whether hemolysis has occurred, a number of tests have been developed to determine hemoglobin (Hb) levels in a blood sample. One common reagent used for determining Hb levels or hemolysis in a blood sample is referred to as Drabkin's Reagent. Drabkin's Reagent comprises a mixture that works by lysing red blood cells and quantitatively converting all Hb in a sample into one form, cyanomethaemoglobin, which is then be measured on a spectrometer using a single wavelength. As such, Drabkin's Reagent measures intracellular hemoglobin as well as free hemoglobin. For at least this reason, Drabkin's Reagent does not provide a realistic picture of the extent of free Hb present at a particular point in time in a sample, which is indicative of hemolysis. The most common way to determine hemolysis is to use a centrifuge to spin down a blood sample, therein producing a method of qualitative assessment for the resulting plasma layer. This is generally sufficient in the laboratory setting.

Sampler caps exist that are used in a point of care environment for de-aerating blood samples while sealing a sampler to prevent inadvertent leakage of the blood sample. See for example U.S. Pat. No. 7,896,818. Such sampler caps have an inlet for connecting to a syringe, and an outlet that allows an analyzer probe to be extended through the sampler cap for obtaining a blood sample from the sampler. These sampler caps, however, do not have any mechanism for testing the blood sample prior to the introduction of the blood sample into the analyzer.

A need exists, therefore, for rapid testing of a fluid sample while also making the fluid sample seamlessly available for further testing within a testing instrument, such as an analyzer. It is to such an improved device and method that facilitates rapid and accurate multi-testing of the fluid sample that the present disclosure is directed.

BRIEF DESCRIPTION OF THE DRAWINGS

The accompanying drawings, which are incorporated in and constitute a part of this specification, illustrate one or more implementations described herein and, together with the description, explain these implementations. In the drawings:

FIG. 1 illustrates an exploded view of a fluid testing device removably attachable to a fluid housing such as a syringe constructed in accordance with one embodiment of the present disclosure.

FIG. 2 illustrates a perspective view of the fluid testing device of FIG. 1, and constructed in accordance with one embodiment of the present disclosure.

FIG. 2A is a perspective view of another embodiment of a fluid testing device connected to a fluid collection device such as a vacutainer in accordance with embodiments of the present disclosure.

FIG. 3 illustrates a top plan view of the fluid testing device of FIG. 1, and constructed in accordance with one embodiment of the present disclosure.

FIG. 10 illustrates an exploded view of a fluid testing device removably attachable to a fluid housing, such as a syringe, and constructed in accordance with one embodiment of the present disclosure.

FIG. 11 illustrates a perspective view of another embodiment of a fluid testing device constructed in accordance with the present disclosure.

FIG. 17 illustrates a perspective view of a blood testing device having a closeable gate constructed in accordance with one embodiment of the present disclosure.

FIG. 18 illustrates the blood testing device of FIG. 11 having the closeable gate in a first position.

FIG. 19 illustrates the blood testing device of FIG. 11 having the closeable gate in a second position.

DETAILED DESCRIPTION

Figure 4A:
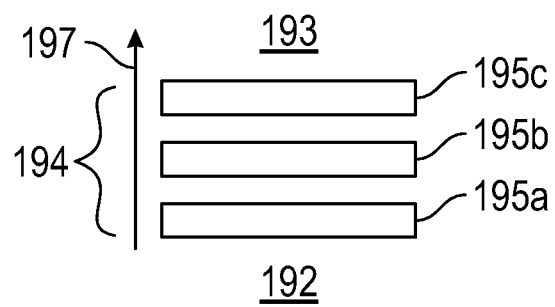
FIG. 4A is a diagrammatic view of a lateral flow membrane being a multi-layer structure in accordance with embodiments of the present disclosure.

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, may be analog and/or digital, components, or one or more suitably programmed microprocessors and associated hardware and software, or hard-wired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transitory memory. Exemplary non-transitory memory includes random access memory, read only memory, flash memory or the like. Such non-transitory memory may be electrically based or optically based.

The term "sample" as used herein refers to any fluid that can be removed from a source of fluid, and that may be subject to multiple tests. In one embodiment, the term sample refers to a bodily fluid from a mammal, such as blood, saliva or urine. Other types of samples include water from a source such as a river, pool or the like.

The term "matrix" as used herein refers to a material in which something can be enclosed or embedded. An example of a "matrix" includes a lateral flow membrane designed as a filter to separate a first constituent part such as red blood cells from a second constituent part such as plasma. A matrix can also be constructed of a backing material having spaced apart microposts to form a filter capable of separating the first constituent part from the second constituent part.

In accordance with one aspect, there are provided devices, systems, and processes for determining a presence of hemolysis in a sample. Advantageously, devices, systems, and processes described herein that test a fluid sample that has been collected from a source via a fluid collection device having a fluid housing, such as a syringe, and present the fluid sample for further assessment to a testing instrument, such as an analyzer. In some embodiments, the device may determine whether hemolysis has occurred in the fluid sample based upon a colorimetry assessment of a portion of the sample.

In accordance with another aspect, there are provided devices, systems, and processes for testing a fluid sample obtained by a fluid collection container.

In accordance with another aspect, there are provided fluid collection devices, systems, accessories and processes having a plasma separating feature.

In accordance with another aspect, there are provided fluid collection devices, systems, accessories, and processes having a hemolysis indicating feature.

In accordance with another aspect, there are provided fluid collection devices, systems, accessories and processes that can determine the presence and/or a concentration of one or more analyte within a sample, such as blood or urine or other fluid. These fluid devices, systems, accessories and processes can be used for a variety of purposes, such as to determine blood type, pathological analysis, glucose levels, determine pregnancy, or the like.

Referring now to the Figures and in particular to FIG. 1, shown therein is a lateral flow testing device 100 constructed in accordance with the present disclosure having a fluid collection device 101 having a fluid housing 102, a first fluid reservoir 104 encompassed at least partially by the fluid housing 102, and a fluid treatment module 106. As will be explained below, the fluid treatment module 106 of the lateral flow testing device 100 includes a means for testing a fluid sample within the fluid treatment module 106. The means for testing may be implemented in a variety of manners discussed herein that conducts a test upon the fluid sample. Exemplary means for testing include lateral flow strips (that are treated with a reagent or devoid of a reagent) filters, matrix materials or the like, sensors (e.g., electrochemical sensors) or the like. The means for testing may be read by a suitable reader, such as a camera, electrical circuit or the like. The construction of the reader will depend upon the type of data generated by the means for testing. In some embodiments, the means for testing includes a means for adding a constituent to the fluid sample; and/or a means for removing a constituent from the fluid sample. The means for adding the constituent to the fluid sample includes a substance or mixture, e.g., a reagent, for use in chemical analysis or other reactions. When the fluid sample is blood, the constituent can be plasma devoid of red blood cells. The means for removing may include a device for the active or passive separation of the constituent. Active separation devices include one or more transducer generating a medium applied to the fluid sample to separate the constituents of the fluid sample. The transducer can work on the principle of magnetics; acoustics; or dielectrophoretics. See Optofluidic sensor for inline hemolysis detection on whole blood, ACS Sens. 2018, 3, 4, 784-791. Publication Date Feb. 23, 2018.

Passive separation devices include lateral flow strips, paper filters, matrices, micro capillaries and the like that physically separate at least one of the constituents from the fluid sample.

In the example shown in FIG. 1, the fluid treatment module 106 is provided with a lower portion 108, an upper portion 110, a second fluid reservoir 111, a testing device, such as a lateral flow strip 112, a fluid channel 114, a first fluid port 116, a second fluid port 118, an optical zone 120, and a bar code 122. Although one testing device, such as the lateral flow strip 112 is shown in FIG. 1, it should be understood that the fluid treatment module 106 can be provided with multiple testing devices within a volume encompassed by the lower portion 108 and/or the upper portion 110. In this embodiment, each of the testing devices may be configured to conduct a predetermined test for a different analyte/condition.

The fluid housing 102 is constructed so that the fluid housing 102 can hold and contain a fluid sample such as blood containing blood cells suspended within plasma. The fluid collection device 101 can be a syringe having a piston 102a within the fluid housing 102 so as to define the first fluid reservoir 104 or a vacutainer, for example. The fluid housing 102 can be a part of the syringe or the vacutainer, for example. The fluid collection device 101 can be used to obtain the fluid sample from a fluid source, such as an animal or other liquid source (add a urine example and a blood example—test for heart attack, drug use, pre-MRI testing (determine pregnancy or a heart attack) and stored within the fluid housing 102. For example, blood may be collected from an animal, such as a human, or a non-human (such as a cat, dog, cow, horse, fish, or the like).

The lower portion 108 and the upper portion 110 of the fluid treatment module 106 can be tubular devices that are sealably connected to form a housing that encompasses the second fluid reservoir 111. The lower portion 108 has the first fluid port 116 formed in an upper wall of the lower portion 108. The lower portion 108 and the upper portion 110 can be constructed of fluid impermeable materials, such as plastic using any suitable manufacturing process, such as 3D printing or injection molding. When the fluid treatment module 106 is connected to the fluid housing 102, a fluid sample may be transferred from the first fluid reservoir 104 to the second fluid reservoir 111. Once in the second fluid reservoir 111, a portion of the fluid sample may be directed through the second fluid port 118 into the fluid channel 114 containing the lateral flow strip 112. The second fluid port 118 may be formed in the lower portion 108. Once in the fluid channel 114, the fluid sample passes through the lateral flow strip 112 or other type of membrane or filter paper to enter an analysis portion 123 of the lateral flow strip 112 or membrane or filter paper. The lateral flow strip 112 or membrane or filter paper or the like can add a constituent to the fluid sample, can remove a constituent from the fluid sample or add a first constituent to the fluid sample and remove a second constituent from the fluid sample. For example, the lateral flow strip 112 can be untreated with a reagent and remove a constituent, such as red blood cells, from the fluid sample. Or, the lateral flow strip or membrane or filter paper can be treated with a reagent that is then added to the fluid sample as the fluid sample passes through the lateral flow strip 112. As another example, the lateral flow strip 112 may be a filter adapted to separate red blood cells from plasma and be treated with a reagent. In this case, the reagent is added to the plasma as the plasma is passed to the analysis portion 123. The lateral flow strip 112 can also be treated with the reagent so that the reagent mixes with the plasma as the plasma passes through the lateral flow strip 112 to the analysis portion 123. In some embodiments, the lateral flow strip 112 may use capillary action (which may also be referred to as capillary flow) and/or size exclusion techniques, such as filter paper, to cause the separation of constituents in the fluid sample such as blood cells and plasma if the fluid sample is a blood sample as described more fully in U.S. patent application Ser. No. 15/317,748, the entirety of which is incorporated herein by reference. The analysis portion 123 of the lateral flow strip 112 may be placed adjacent to the optical zone 120. The optical zone 120 is a portion of the lower portion 108 that is transparent to light of a predetermined spectrum so that the analysis portion 123 can be read through the optical zone 120. In some embodiments, the predetermined spectrum is visible light. When the action caused by the lateral flow strip or the like is separation of the blood into plasma, the plasma that has passed through the lateral flow strip 112 may then be analyzed colorimetrically in the optical zone 120 to determine a degree of hemolysis using an optical reader or human eyes. Exemplary degrees of hemolysis include none (plasma has a yellowish color and generally less than 25 milligram/deciliter of hemolysis) slight (plasma has an orangish color and has hemolysis generally between 25 milligram/deciliter to 150 milligram/deciliter), moderate (plasma has a reddish color and hemolysis is generally between 150 milligram/deciliter to 300 milligram/deciliter) and gross (generally above 300 milligram/deciliter). The optical reader may be a part of a point of care analyzer, or a camera and software of a smart phone, or the like. In some embodiments, the lateral flow strip 112 or membrane or filter paper or the like may have one or more reagent in a path from the second fluid port 118 to the analysis portion 123. In these embodiments, the reagent(s) may react with the sample so as to cause a predetermined change (e.g., color) that may be detected in the analysis portion of the lateral flow strip 112. For instance, it may be important to pre-analyze a sample for certain drugs or diseases.

There are many advantages of using the embodiments of the inventive concepts disclosed herein, such as the fluid collection device 101 and the fluid treatment module 106, such as improved sanitation, timing, and consistency due to the enclosed nature and predetermined fluid paths. For example, the lateral flow strip 112 can be treated with a reagent suitable for conducting a pregnancy test. The reagent may be configured to detect a hormone named human chorionic gonadotropin (HCG) in urine. The patient may collect a urine sample in a cup, and then draw a sample of the urine with the fluid collection device 101. After the sample of urine is drawn, the patient may then connect the fluid treatment module 106 to the fluid collection device 101 to form a fluid tight assembly such that urine will not be spilled. As the urine passes into the fluid treatment module 106, the urine will mix with the reagent thereby causing a reaction that may be monitored to determine whether the patient is pregnant. This avoids having to apply a wand treated with the reagent into a urine stream, or sloshing the wand within the cup as accomplished in conventional pregnancy tests.

In another example, a patient may present with symptoms indicative of a stroke. Prior to providing a contrast MRI for the patient, the health care provider may ask the patient if the patient is pregnant or has kidney problems, but the patient may not be able to answer these questions in a reliable manner. The health care provider will then likely obtain a sample from the patient to test for an analyte, such as creatinine, that is indicative of the patient's kidneys not functioning properly or hCG to determine pregnancy. The sample can be blood or urine. In this case, the lateral flow strip 112 may be treated with a reagent configured to test for pregnancy. After the health care provider obtains the sample with the fluid collection device 101, the health care provider will connect the fluid treatment module 106 to the fluid collection device 101 to form a fluid tight assembly. As the sample passes into the fluid treatment module 106, the sample will mix with the reagent on the lateral flow strip 112, for example, thereby causing a reaction that may be monitored to determine whether the patient is pregnant. A portion of the sample may then be drawn from the fluid treatment module 106 by an analyzer to test for creatinine, for example, by inserting a probe or pipette from the analyzer through the third connector portion 130. In this manner, the health care provider can test/verify that the patient is not pregnant and that the patient's kidneys are functioning properly in a sanitary manner by conducting the pregnancy test as a part of the work flow for testing for creatinine.

In other embodiments, one or more analyte sensors 124 may be positioned within the fluid channel 114 and positioned to interact with the fluid sample passing through the fluid channel 14. The analyte sensors 124 can be electrochemical sensors, such as potentiometric sensors, amperometric sensors and combinations thereof.

To facilitate directing the fluid sample into the second fluid port 118, the lower portion 108 and/or the upper portion 110 may have a removable cap or gas permeable/fluid impermeable membrane sealing the first fluid port 116 (not shown), for instance, that temporarily prevents movement of the fluid sample through the first fluid port 116. When the fluid sample has been analyzed using the lateral flow testing device 100, the cap may be removed and the fluid sample may be allowed to pass through the first fluid port 116 to be used for further testing, for instance, as desired. The gas permeable/fluid impermeable membrane covering the first fluid port 116 may pass air out of the fluid sample to de-aerate the fluid sample.

As described above, the bar code 122 may be positioned on an exterior surface of the upper portion 110, and used to identify the fluid sample, the patient that the fluid sample belongs too, the geographic area the fluid sample was collected from (e.g. river), the test to be performed, and the like.

In one use, the fluid collection device 101 can be used to obtain a fluid sample from an animal and to deposit the fluid sample within the fluid housing 102. When the fluid housing 102 is a syringe having a needle, the needle can then be removed to expose a first connector portion 126 of the fluid housing 102. The first connector portion 126 can be any suitable type of connector, such as a Luer connector, a male port, or a female port. Then, a second connector portion 128 of the lower portion 108 can be connected to the first connector portion 126, and a portion of the fluid sample directed from the first fluid reservoir 104 to the second fluid reservoir 111. Once in the second fluid reservoir 111, the removable cap, or gas permeable/fluid impermeable membrane may prevent the flow of the fluid sample through the first fluid port 116. As pressure builds within the second fluid reservoir 111, a portion of the fluid sample may be directed through the second fluid port 118 into the fluid channel 114 containing the lateral flow strip 112. The second fluid reservoir 111 and the fluid channel 114 are separated by a fluid impermeable wall 129 having the second fluid port 118. The second fluid port 118 may be spaced a distance from the optical zone 120 so that the fluid sample passes through a substantial amount of the lateral flow strip 112 prior to reaching the analysis portion 123, or the optical zone 120. The analyte sensors 124 are positioned between the second fluid port 118 and the optical zone 120. Readings can then be taken in the optical zone 120, or from the analyte sensors 124. For example, if the lateral flow strip 112 or membrane or filter paper is configured to separate red blood cells from plasma, the red blood cells may be separated from the plasma prior to the plasma entering the analysis portion 123 and be read to determine an extent of hemolysis. The extent of hemolysis can be determined by the color of the plasma. That is, plasma that is pink or red may be determined to have hemolyzed, and plasma that is colorless, yellow or light orange (none to slight hemolysis) may be determined to have not hemolyzed to an extent to prevent further analysis. A color reference chart may be provided on the exterior surface of the fluid treatment module 106. In any event, if the testing occurring within the lower portion 108 indicates that further testing may be accomplished, then the fluid sample may be transferred through a third connector portion 130 of the upper portion 110 to a blood gas analyzer or other suitable testing instrument for additional testing. Suitable testing instruments may include urine analyzers, blood analyzers, or the like. In certain cases, a pipette (also known as a "probe") (not shown) may be introduced through the third connector portion 130 to obtain a portion of the sample from within the first fluid reservoir 104 or the second fluid reservoir 111. The third connector portion 130 can be a luer connector, a male port, a female port of the like. The bar code 122 can be read by an optical reader and entered into a medical software program to track the results of one or more tests occurring within the lower portion 108 or by the blood gas analyzer or other suitable testing instrument.

In some embodiments, the housing has a longitudinal axis 132 extending between the upper portion 110 and the lower portion 108, and the lateral flow strip 112 has a major axis 134 extending in a non-parallel relationship with the longitudinal axis 132. In the example shown in FIG. 1, the major axis 134 of the lateral flow strip 112 can be substantially perpendicular to the longitudinal axis 132. The lateral flow strip 112 can be constructed in a variety of manners. For example, the lateral flow strip 112 can be a lateral flow membrane or matrix that filters the first constituent (e.g., red blood cells) of the sample from a second constituent (e.g., plasma). The lateral flow strip 112 may have a distal end 136 in the optical zone 120 and a proximal end 138 away from the optical zone 120. The distal end 136 and/or the proximal end 138 may be treated with a reagent.

FIG. 2 illustrates a lateral flow testing device 140 including a fluid collection device 141 having a fluid housing 142, a fluid treatment module 144 encompassed by the fluid housing 142, a first fluid reservoir 146, and a second fluid reservoir 148. The lateral flow testing device 140 is similar to the lateral flow testing device 100 described above, therefore, in the interest of brevity only the differences will be described herein. The fluid collection device 141 and the fluid treatment module 144 are integrated into a unitary structure in which the fluid housing 142 encompasses the first fluid reservoir 146 and the second fluid reservoir 148. Further, the third connector portion 130 is used for the inflow of the fluid sample into the fluid collection device 141 and also used to draw the fluid sample from the first fluid reservoir 146 and/or the second fluid reservoir 148.

FIG. 2A illustrates a lateral flow testing device 140a including a fluid collection device 141a having a fluid housing 142a, a fluid treatment module 144a connected to the fluid housing 142a, a first fluid reservoir 146a, and a second fluid reservoir 148a. The lateral flow testing device 140 is similar to the lateral flow testing device 100 described above, therefore, in the interest of brevity only the differences will be described herein. In the embodiment shown in FIG. 2A, the fluid collection device 141 is a vacutainer, and the fluid treatment module 144 has a second connector portion 128a in the form of a needle 150 extending through a septum 152 of the fluid collection device 141. To draw the fluid sample into the second fluid reservoir 148 from the first fluid reservoir 146, the fluid treatment module 144 may include a negative pressure device 154 in fluid communication with the second fluid reservoir 148. The negative pressure device can be a bellows used to create the negative pressure, or a vacuum port that is connectable to a vacuum source.

FIG. 3 illustrates a top plan view of a fluid treatment module 160 similar to fluid treatment modules 106 and 144. In this embodiment, the fluid treatment module 160 is provided with a fluid channel 162 that connects a first fluid port 164 with a second fluid port 166 to direct a flow of a fluid sample into a fluid channel 168 for separation of the fluid sample into at least two constituent parts, for testing by way of one or more analyte sensors as described above. For instance, when the fluid sample is blood, the lateral flow strip 112 housed in the fluid channel 168 functions to separate the blood cells from the plasma so that the plasma is visible in the optical zone 120. The fluid impermeable wall 129 may fluidly isolate the fluid channel 168 from the first fluid port 164, with the exception of the fluid channel 162.

Figure 4:
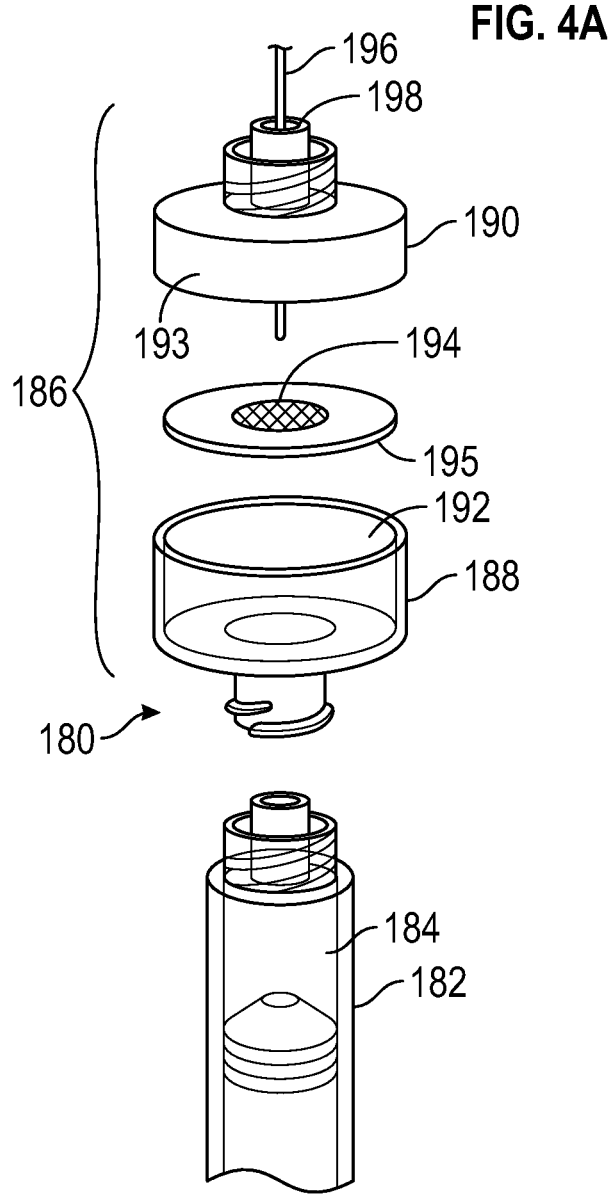
FIG. 4 illustrates an exploded view of a fluid testing device removably attachable to a fluid housing, such as a syringe, and constructed in accordance with one embodiment of the present disclosure.

Referring now to FIG. 4, shown therein is another embodiment of a lateral flow testing device 180 having a fluid housing 182, a fluid reservoir 184, and a fluid treatment module 186. The fluid housing 182 can be identical in construction and function as the fluid housing 102 discussed above. The fluid treatment module 186 of the lateral flow testing device 180 is provided with a lower portion 188, an upper portion 190, a second fluid reservoir 192 defined by the lower portion 188, a third fluid reservoir 193 defined by at least a portion of the upper portion 190, and a lateral flow membrane 194. The lateral flow membrane can be similar in construction and function as the lateral flow strip 112 discussed above.

The lower portion 188 and the upper portion 190 of the fluid treatment module 186 are sealably connected to form the second fluid reservoir 192 and the third fluid reservoir 193 separated by the lateral flow membrane 194. When the fluid treatment module 186 is connected to the fluid housing 182, a fluid sample may be transferred from the first fluid reservoir 184 to the second fluid reservoir 192 and through the lateral flow membrane 194 into the third fluid reservoir 193. As the fluid sample is transferred from the second fluid reservoir 192 to the third fluid reservoir 193, the fluid sample passes through the lateral flow membrane 194 and the fluid sample is separated into at least two constituent parts, e.g., blood cells remain in the second fluid reservoir 192 or are captured within the lateral flow membrane 194, and plasma passes through the lateral flow membrane 194 and into the third fluid reservoir 193.

As shown in FIG. 4A, the lateral flow membrane 194 may be a multi-layer structure, with each layer performing a separate function to the sample as the sample passes sequentially through the layers. For example, as shown in FIG. 4A, the lateral flow membrane 194 may have three layers 195a, 195b, and 195c. The layer 195a may be a mesh configured to divert bubbles within the sample into a hollow chamber. For instance, layer 195a may be an asymmetric membrane which diverts gas within the sample into the hollow chamber, and allows liquid within the sample to pass through. The layer 195b may be a material suitable to separate red blood cells from plasma as well as separating any clots or particulate matter from the plasma. Any one or more of the layers 195a, 195b, or 195c can be provided with one or more analyte regions that receive the sample and mixes an analyte with a portion of the sample to provide an indication of the presence and/or concentration of certain analytes within the sample. The liquid portion of the sample can pass sequentially through the layers 195a, 195b and 195c as indicated by arrow 197. In some embodiments, the layer 195c may also be provided with one or more electrochemical sensor (not shown) to provide further analysis of the sample.

Referring again to FIG. 4, at least the upper portion 190 of the fluid treatment module 186 may be constructed of an optically clear material which allows the fluid that has passed through the lateral flow membrane 194 to be colorimetrically analyzed in the third fluid reservoir 193 using an optical reader, as described above or human eyes. Because the fluid can be analyzed with human eyes, the fluid treatment module 186 allows a fluid sample to be analyzed at a point-of-care without the need for additional devices and is non-disruptive to standard fluid collection workflow. This point-of-care review prevents or reduces pre-analytical errors, such as hemolyzed blood for instance, due to sample handling.

Also shown in FIG. 4 is a probe 196 which may be attached to or part of a testing instrument or fluid analysis machine (not shown) such as a blood gas analyzer when the sample is blood. Where whole blood is needed for analysis, the probe 196 may be passed through a fluid port 198 in the fluid treatment module 186, through the third fluid reservoir 193, and through the lateral flow membrane 194 into the second fluid reservoir 192 where the fluid sample has not been separated. It should be noted that in some embodiments the fluid treatment module 204 is sized such that the probe 196 does not pass through the second fluid reservoir 192 and thus draws a sample of fluid from the second fluid reservoir 192, rather than the first fluid reservoir 184.

Figure 5:
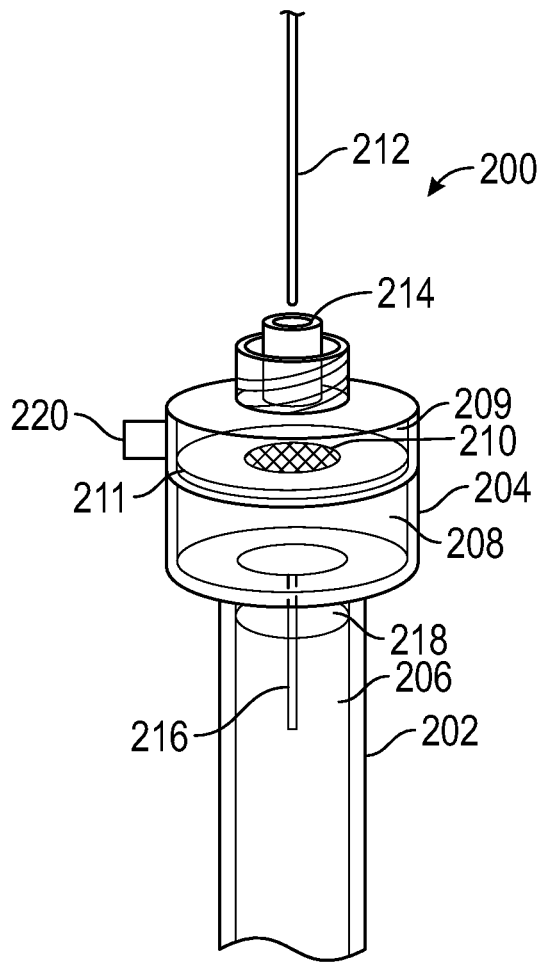
FIG. 5 illustrates a perspective view of another embodiment of a fluid testing device constructed in accordance with the present disclosure.
Figure 8:
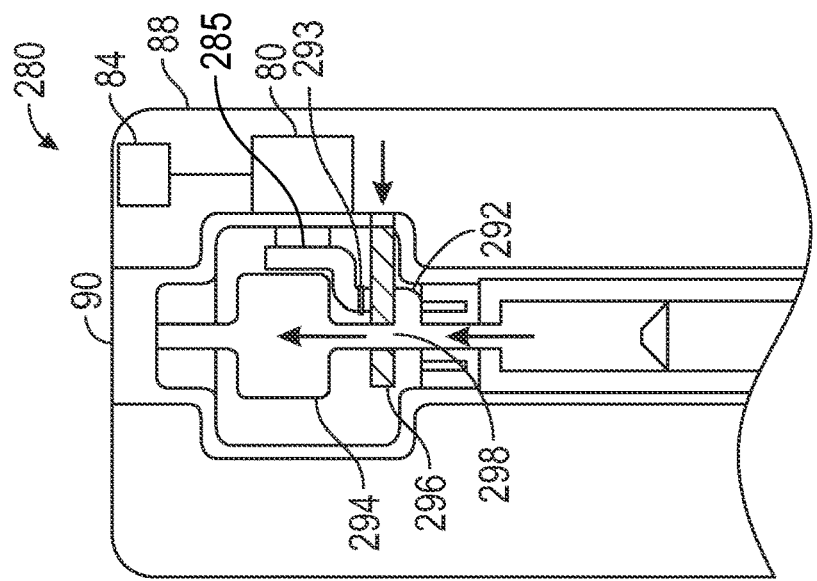
FIG. 8 illustrates the fluid testing device of FIG. 6 having the moveable gate in a second position.
Figure 7:
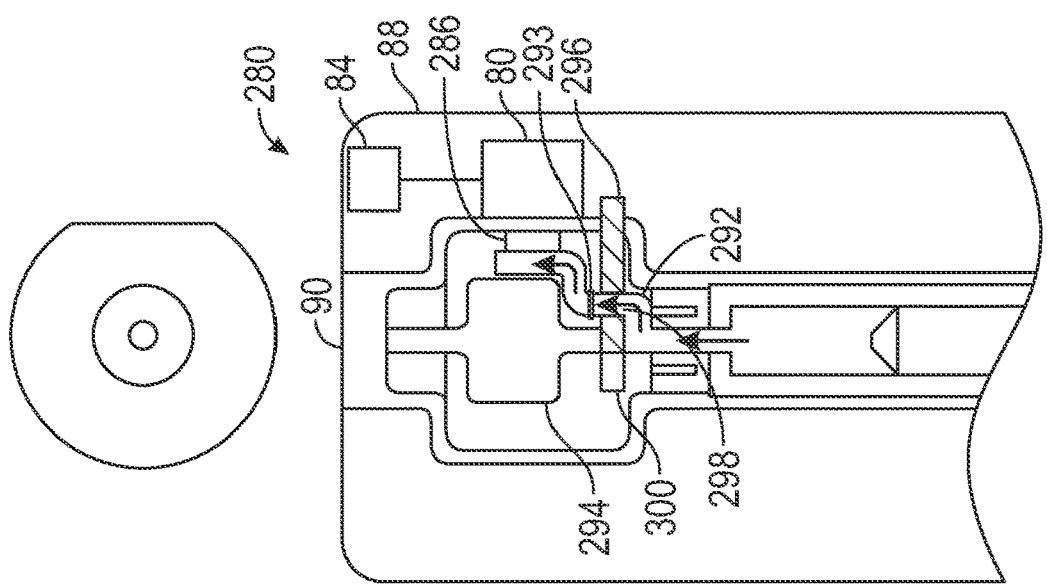
FIG. 7 illustrates the fluid testing device of FIG. 6 having the moveable gate in a first position.
Figure 6:
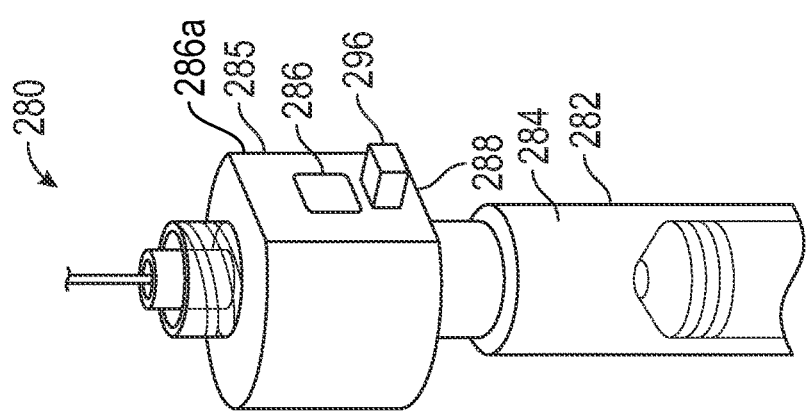
FIG. 6 illustrates a perspective view of a fluid testing device having a moveable gate constructed in accordance with one embodiment of the present disclosure.
Figure 9B:
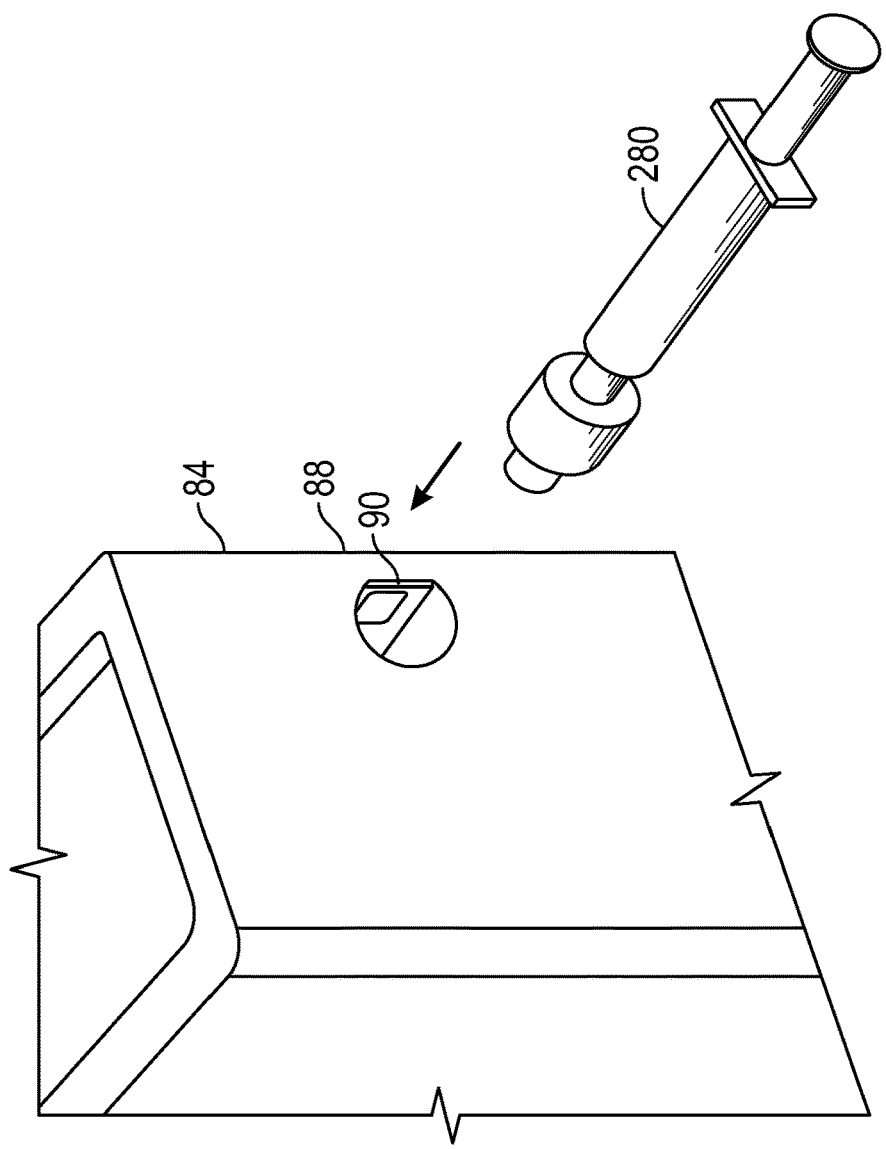
FIGS. 9A and 9B illustrate a fluid housing of FIG. 6 being inserted into an analysis unit for fluid analysis in accordance with embodiments of the present disclosure.
Figure 9A:
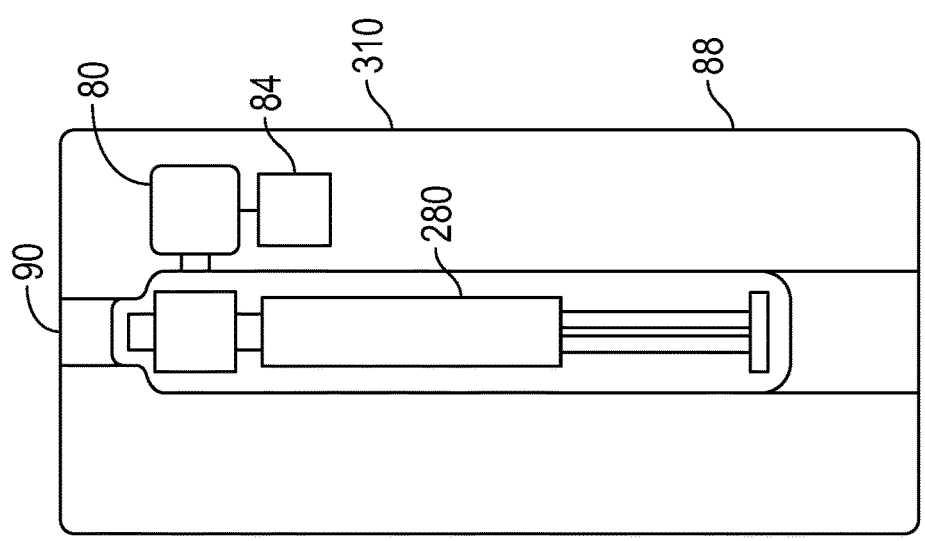

FIG. 5 illustrates another version of a lateral flow fluid testing device 200 having a fluid collection device 201 having a fluid housing 202, a fluid treatment module 204, a first fluid reservoir 206, a second fluid reservoir 208, a third fluid reservoir 209, a lateral flow membrane 210, and a fluid port 214. The lateral flow fluid testing device 200 is similar to the lateral flow fluid testing device 180 described above, therefore, in the interest of brevity only the differences will be described herein. In the embodiment shown in FIG. 2A, the fluid collection device 201 is a vacutainer, and the fluid treatment module 204 has a connector portion 216 in the form of a needle extending through a stopper 218 of the fluid collection device 141. To draw the fluid sample into the second fluid reservoir 208 from the first fluid reservoir 206, the fluid treatment module 204 may include a negative pressure device 220 in fluid communication with the third fluid reservoir 209. The negative pressure device 220 can be a bellows used to create the negative pressure, or a vacuum port that is connectable to a vacuum source (not shown).

A probe 212 is also shown which may be attached to or part of a testing instrument or fluid analysis machine (not shown) such as a blood gas analyzer. Where whole blood is needed for analysis, the probe 212 may be passed through the fluid port 214 in the fluid treatment module 204, through the third fluid reservoir 209, and through the lateral flow membrane 210 into the second fluid reservoir 208 where the blood sample has not been separated. The fluid treatment module 204 may be sized such that the probe 212 does not pass through the second fluid reservoir 208 but draws a fluid sample from fluid in the second fluid reservoir 208, rather than the first fluid reservoir 206. In some embodiments, the probe 212 may be passed into and used to draw the fluid sample from the third fluid reservoir 209.

Referring now to FIGS. 6-9B, shown therein is another embodiment of a fluid testing device 280 that can be read by a reader 80 and/or utilized to separate the fluid sample into at least two constituent parts. When the fluid sample is blood, the fluid testing device 280 can separate the blood into a first constituent part having plasma having a concentration of red blood cells higher than a concentration of red blood cells in the blood; and a second constituent part having plasma that is substantially devoid of red blood cells. The fluid testing device 280 is provided with a fluid housing 282, a fluid reservoir 284, a fluid treatment reservoir 285, an optical zone 286 on an exterior wall 286a of the fluid housing 282, a treatment window 288 on the exterior wall 286a of the fluid housing 282, a first flow path 292, a lateral flow membrane 293 within the first flow path 292, a second flow path 294 separate from the first flow path 292, a gate 296 having a port 298, and a gate guide channel 300. The gate 296 is positioned within the gate guide channel 300 and can be moved in any suitable direction (such as laterally), as described below to guide the fluid sample into the first flow path 292 or the second flow path 294.

When the gate 296 is in a first position (shown in FIG. 7), a fluid sample is directed into the first flow path 292 and through the lateral flow membrane 293 such that the fluid sample is separated into at least two constituent parts and a separated fluid sample is directed into the optical zone 286 where the separated fluid sample may be read with the reader 80. The lateral flow membrane 293 can be similar in construction and function as the lateral flow strip 112. When the reader 80 is an optical reader and the fluid sample is a blood sample, a degree of hemolysis can be determined by a control unit 84 based upon a colorimetric analysis of the separated fluid sample. That is, when the separated fluid sample (plasma in the case of a blood sample) is devoid of hemolysis, the plasma will be substantially devoid of any color, i.e., the sample will be transparent. When hemolysis has occurred within the separated fluid sample, the plasma will be pink. By correlating the color of the plasma with predetermined colors indicative of an extent of hemolysis occurring within other samples, the extent of hemolysis within the separated fluid sample can be determined. The fluid sample, including but not limited to blood, can be tested for one or more analytes as discussed above with respect to the discussion regarding the lateral flow strip 112.

The reader 80 may be provided with an optical reader (not shown). When the fluid testing device 280 is inserted into the reader 80, the optical reader of the reader 80 has a field of view directed to the optical zone 286 where the fluid sample may be read. The lateral flow membrane 293 separates the fluid sample such that only the separated fluid sample is visible in the optical zone 286. Then the optical reader captures an image of the separated fluid sample and any backdrop and sends the image to the analysis unit 84 for colorimetric analysis as discussed above. The analysis unit 84 may be provided with further fluid analysis features (not shown) such as gas analysis which may further analyze the fluid sample after it passes through the second flow path 294.

The reader 80 may be portable and have a housing 88 that includes a slot 90 sized and dimensioned to receive the fluid testing device 280 such that the optical zone 286 is in the field of view of the optical reader. The housing 88 can be provided in a variety of shapes such as a hot dog bun, for instance. The analysis unit 84 can be supported in the housing 88 or be separate therefrom. For example, the reader 80 can be provided with a wireless transceiver to communicate with the analysis unit 84.

Once the fluid sample has been analyzed, the gate 296 may be moved to a second position (shown in FIG. 8), which moves the port 298 into the second flow path 294 allowing the fluid sample to pass into the second flow path 294.

FIG. 10 illustrates a lateral flow fluid testing device 350 having a fluid housing 352, a first fluid reservoir 354, and a fluid treatment module 356. The fluid treatment module 356 of the lateral flow testing device 350 is provided with a lower portion 358, an upper portion 360, a second fluid reservoir 362, a third fluid reservoir 363, and a lateral flow membrane 364 inset in a third fluid port 365 of a fluid impermeable divider 366.

The lower portion 358 and the upper portion 360 of the fluid treatment module 356 are sealably connected to form the second fluid reservoir 362 and the third fluid reservoir 363 separated by the fluid impermeable divider 366. When the fluid treatment module 356 is connected to the fluid housing 352, a fluid sample may be transferred from the first fluid reservoir 354 to the second fluid reservoir 362 and through the lateral flow membrane 364 into the third fluid reservoir 363. As the fluid sample is transferred from the second fluid reservoir 362 to the third fluid reservoir 363, the fluid sample passes through the lateral flow membrane 364 and the fluid sample is separated into at least two constituent parts, e.g., blood cells remain in the second fluid reservoir 362 and plasma passes through the lateral flow membrane 364 and into the third fluid reservoir 363.

At least the upper portion 360 of the fluid treatment module 356 is constructed of an optically clear material which allows the fluid that has passed through the lateral flow membrane 364 to be colorimetrically analyzed in the third fluid reservoir 363 using an optical reader as described above or human eyes.

Also shown in FIG. 10 is a probe 367 which may be attached to or part of a testing instrument or fluid analysis machine (not shown) such as a blood gas analyzer. Where whole blood is needed for analysis, the probe 367 may be passed through a fluid port 368 in the fluid treatment module 356, through the third fluid reservoir 193, and through the lateral flow membrane 364 into the second fluid reservoir 362 where the blood sample has not been separated. It should be noted that the fluid treatment module 356 may be sized such that the probe 367 does not pass through the second fluid reservoir 362 and thus draws a sample of fluid from the second fluid reservoir 362.

The fluid impermeable divider 366 may further be provided with at least one reagent 370 (only one of which is designated in FIG. 10) that allow further testing of a fluid sample. For instance, reagents 370 may be used to determine blood type, pathological analysis, glucose levels, determine pregnancy, etc. While reagents 370 are illustrated only on one side of the fluid impermeable divider 366, it should be noted that reagents 370 may be placed on one side or both sides of the fluid impermeable divider 366. For instance, some reagents may be placed on the side of the second fluid reservoir 362 to test the fluid sample before separation into constituent parts through the lateral flow membrane 364 while others may be place on the side of the third fluid reservoir 363 to test the separated fluid sample. In some embodiments, reagents 370 may be placed on both sides of the fluid impermeable divider 366 to test the fluid sample and the separated fluid sample. Reaction with the reagents may be read by an optical reader as described above or human eyes.

FIG. 11 illustrates another version of a lateral flow fluid testing device 400 having a fluid collection device 401 having a fluid housing 402, a fluid treatment module 404 connected to the fluid housing 402, a first fluid reservoir 406 within the fluid housing 402, a second fluid reservoir 408 within the fluid treatment module 404, a third fluid reservoir 409 within the fluid treatment module 404, a lateral flow membrane 410 separating the second fluid reservoir 408 and the third fluid reservoir 409, and a first fluid port 414. The lateral flow fluid testing device 400 is similar to the lateral flow fluid testing device 350 described above, therefore, in the interest of brevity only the differences will be described herein. In the embodiment shown in FIG. 11, the fluid collection device 401 is a vacutainer, and the fluid treatment module 404 has a second fluid port 415a in the form of a needle 416 extending through a septum 418 of the fluid collection device 401. To draw the fluid sample into the second and third fluid reservoirs 408 and 409 from the first fluid reservoir 406, the fluid treatment module 404 may include a negative pressure device 420 in fluid communication with the third fluid reservoir 409. The negative pressure device 420 can be a bellows used to create the negative pressure, or a vacuum port that is connectable to a vacuum source.

Also shown in FIG. 11 is a probe 412 which may be attached to or part of a testing instrument or fluid analysis machine (not shown) such as a blood gas analyzer. Where whole blood is needed for analysis, the probe 412 may be passed through the fluid port 414 in the fluid treatment module 404, through the third fluid reservoir 409, and through the lateral flow membrane 410 into the second fluid reservoir 408 where the blood sample has not been separated. It should be noted that the fluid treatment module 404 may be sized such that the probe 412 does not pass through the second fluid reservoir 408 and thus draws a sample of fluid from the second fluid reservoir 408. In some embodiments, the fluid treatment module 404 and/or the probe 412 may be sized so as to draw a fluid sample from the first fluid reservoir 406.

Figure 12:
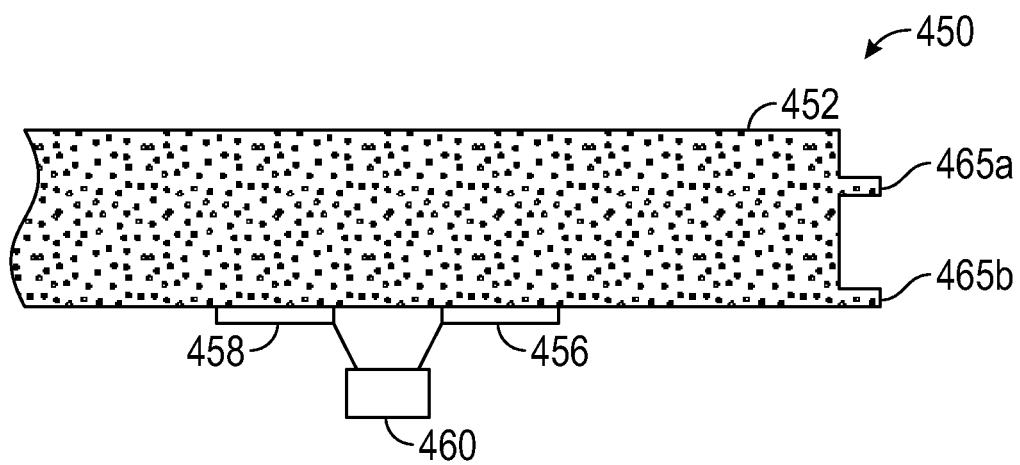
FIG. 12 is a cross sectional view of a portion of a blood testing device constructed in accordance with one embodiment of the present disclosure.
Figure 13:
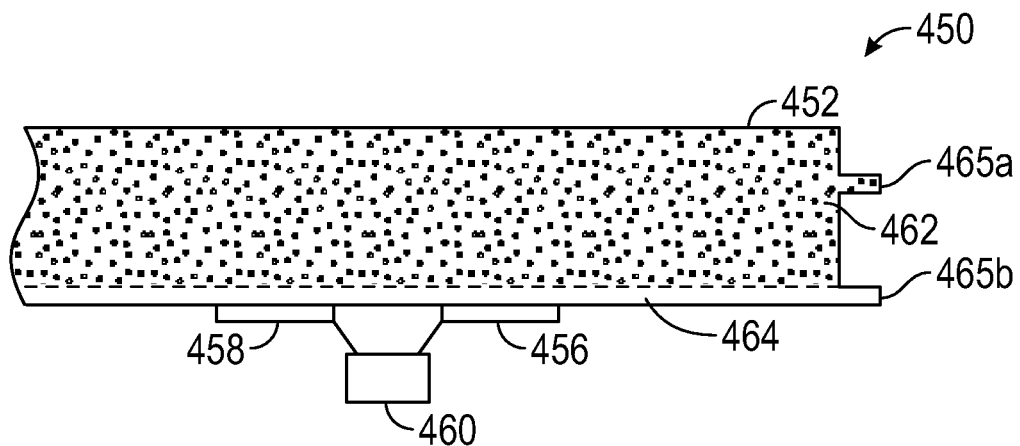
FIG. 13 is a cross sectional view of a portion of the blood testing device of FIG. 12 showing a sample of actively separated blood in accordance with one embodiment of the present disclosure.

Referring now to FIG. 12, shown therein is a diagrammatic view of a testing device 450 (this is a means for separating, removing a component, exemplary, etc.) constructed in accordance with the present disclosure. The testing device 450 can be used for testing blood, or other sample(s) that would benefit from separating two constituent components in the sample. The testing device 450 will be described hereinafter by way of example as a blood testing device. In general, the blood testing device 450 includes a fluid collection device, such as a housing 452, a transducer 456, a reader 458, and a control unit 460 connected to the transducer 456 and the reader 458. The transducer 456 will be described herein by way of example as being an acoustic transducer generating acoustic waves. It should be understood, however, that the transducer 456 can be implemented in other manners to actively separate a sample into a first constituent part (e.g., enhanced red blood cells and plasma) and a second constituent part (e.g., plasma substantially devoid of red blood cells). For example, the transducer 456 can be a magnetic transducer, or a dielectrophoretic transducer. See Optofluidic sensor for inline hemolysis detection on whole blood, ACS Sens. 2018, 3, 4, 784-791. Publication Date Feb. 23, 2018. The power level for the transducer 456 is preferably set at a level that the medium generated by the transducer 456 separates the sample into the first constituent part and the second constituent part without destroying cells or other matter within the sample. The housing 452 is constructed of a fluid impermeable material so that the housing 452 can hold and contain a sample of blood containing blood cells suspended within plasma. The housing 452 can be a syringe or a vacutainer, for example, used for collecting blood and transporting the blood for purposes of testing. The blood may be collected from an animal, such as a human, or a non-human (such as a cat, dog, cow, horse, fish, or the like). The acoustic transducer 456, the reader 458, and the control unit 460 may be located outside of the housing 452 as shown in FIG. 12 or inside the housing 452 (not shown). The acoustic transducer 456 selectively generates acoustic forces that are directed to the housing 452. In some embodiments, the acoustic transducer 456 can be tuned so as to provide a magnitude and/or frequency of acoustic forces so as to facilitate separation of the undamaged blood cells from the plasma and damaged blood cells. The magnitude and/or frequency of the acoustic forces generated by the acoustic transducer 456 can be selected depending upon a size and/or construction of the housing 452, or composition of the blood sample within the housing 452. In one embodiment, the acoustic transducer 456 can be a piezoelectric element. Piezoelectric elements are known to separate plasma from red blood cells. See Optofluidic sensor for inline hemolysis detection on whole blood, ACS Sens. 2018, 3, 4, 784-791. Publication Date Feb. 23, 2018. At least a portion of the housing 452, adjacent to the transducer 456, is constructed of a material that functions to pass the acoustic forces generated by the acoustic transducer 456 into the sample contained within the housing 452. Exemplary materials that can be used to form the housing 452 include glass, crystal, and the like. Parts of the housing 452 away from the transducer 456 can be made of other materials such as plastic. The application of the acoustic forces into the sample by the acoustic transducer 456 causes the blood cells within the blood to move within the plasma to form a first zone 462 having an increased density or concentration of the blood cells than the blood contained prior to the application of the acoustic forces, and at least one second zone 464 being substantially only plasma, i.e., substantially devoid of any undamaged blood cells. The reader 458 is positioned adjacent to the second zone 464 and functions to read at least one parameter of the plasma. In one embodiment, the reader 458 is an optical reader, such as a camera or photospectrometer having a field of view overlapping with the housing 452 such that the plasma within the second zone 464 is visible to the reader 458. In some embodiments, the reader 458 may also include a light source, such as a light emitting diode providing light through the housing 452, a mixer and/or a bar code reader.

The housing 452 may define a first port 465*a* fluidly connected with the first zone 462 to receive the blood having the increased density or concentration of the red blood cells in the plasma, and a second port 465*b* to receive the plasma that is substantially devoid of any red blood cells. The first port 465*a* and/or the second port 465*b* can be connected to a testing instrument or a collection receptacle. The first port 465*a* and the second port 465*b* can be combined within a bifurcated port. One or more testing devices, such as the lateral flow strip 112 can be placed within the first zone 462 or the second zone 464 for separately testing the constituent parts of the blood sample. The testing device(s) may be surrounded with fluid impermeable material so as to isolate the testing device(s) from the blood until a test is desired. At that time, a moveable gate, pierceable membrane or the like can be used to expose the blood sample within the first zone 462 to a first testing device(s), or the blood sample within the second zone 464 to a second testing device(s).

The optical reader 458 is positioned such that the second zone 464 is within the field of view. The control unit 460 selectively actuates/deactuates the acoustic transducer 456 to cause separation of the blood cells and plasma into the first zone 462 and the second zone 464. Then, in some embodiments, the control unit 460 actuates the reader 458 to capture information indicative of at least one parameter of the plasma. The information captured by the reader 458 is then transferred to the control unit 460 to analyze the parameter to conduct at least one predetermined test. Exemplary test(s) include a degree of hemolysis within the sample of blood. Other exemplary tests include HIL (hemolysis, icterus and lipemia) detection, troponin detection, drug detection, pregnancy detection, microclot detection and the like. The control unit 460 can be constructed of circuitry and/or a combination of circuitry and software.

When the reader 458 is the optical reader, the degree of hemolysis can be determined by the control unit 460 based upon a colorimetric analysis of the sample. That is, when the sample is devoid of hemolysis and is illuminated with white light, the plasma will be substantially devoid of any color, i.e., the sample will be transparent. When hemolysis has occurred within the sample, the plasma will be pink when the plasma is illuminated with white light. By correlating the color of the plasma with predetermined colors indicative of an extent of hemolysis occurring within other samples, the extent of hemolysis within the sample can be determined. Depending upon a color of a backdrop, and/or color of illumination of the plasma, colors detected by the reader 18 indicative of an extent of hemolysis may differ.

Information indicative of an extent of hemolysis within the sample can be used to determine whether the blood has hemolysis. As discussed above, other tests may also be conducted by the control unit 460.

Figure 14:
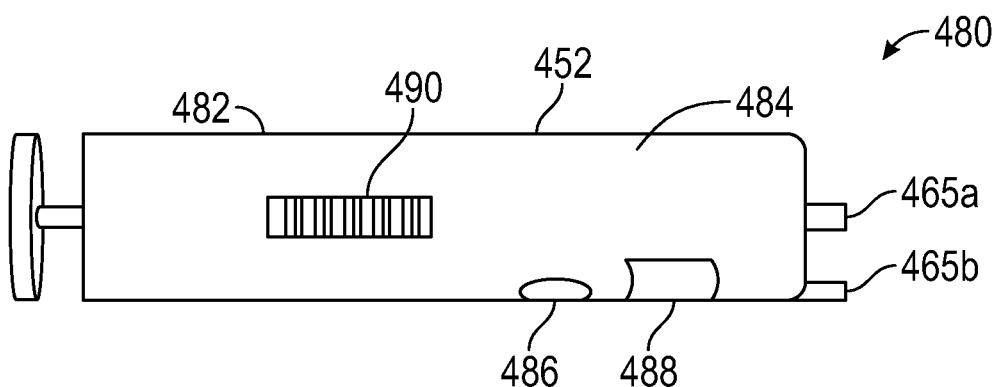
FIG. 14 is an orthogonal view of a fluid collection device having an integrated blood testing device constructed in accordance with the present disclosure.

FIG. 14 illustrates a testing device 480 constructed in accordance with one embodiment of the present disclosure. The testing device 480 can be used for testing blood, or other sample(s) that would benefit from separating two constituent components in the sample. The testing device 480 will be described hereinafter by way of example as a blood testing device. The blood testing device 480 is provided with a fluid container such as a syringe 482 or vacutainer having a fluid reservoir 484 for containing blood. The blood testing device 480 may also be provided with an acoustic transducer 486, an optical zone 488, and a bar code 490 which identifies the contents of the syringe 482 and can be correlated to specific patients. The acoustic transducer 486 may be provided with any suitable shape, such as planar, arcuate, or the like. In some embodiments, the acoustic transducer 486 may be provided with a shape to match a shape of the optical zone 488, or other section of the blood testing device 480 to be stimulated by the acoustic transducer 486. In such an embodiment, the blood testing device 480 allows the blood to be acoustically treated using the acoustic transducer 486 after which the blood may be analyzed using an optical reader or the human eye through the optical zone 488 to conduct one or more predetermined test, such as a degree of hemolysis, HIL detection, troponin detection, drug detection, pregnancy detection, microclot detection or the like. Once a degree of hemolysis within the sample of blood has been determined, for example, a decision can be made whether or not to continue with further testing of the sample of blood.

Figure 15A:
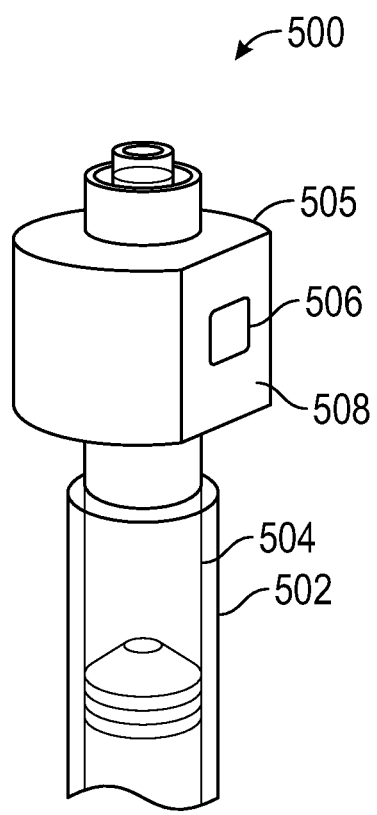
FIGS. 15A-15O illustrate views of portions of another fluid collection device constructed in accordance with the present disclosure.
Figure 15B:
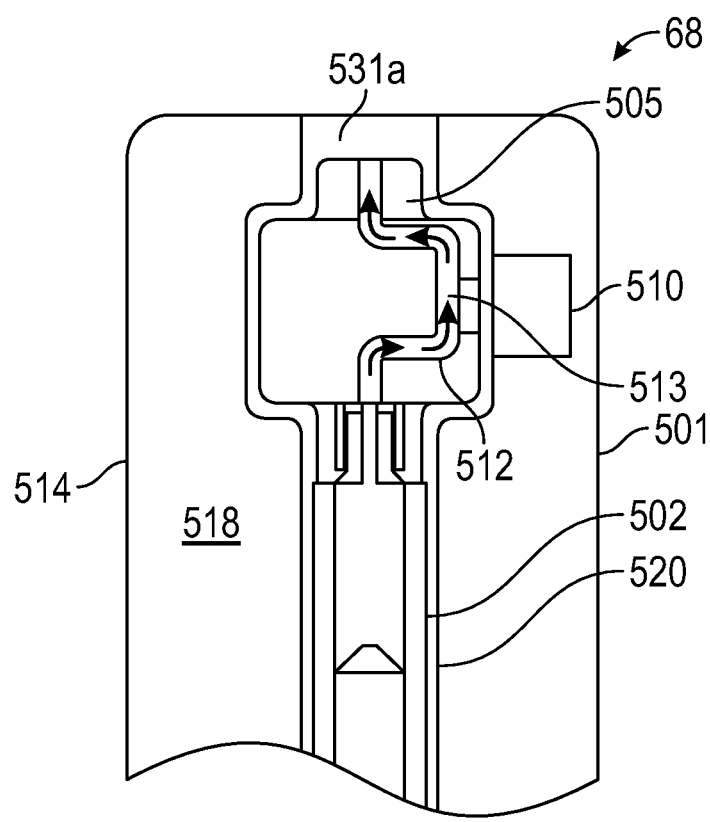
Figure 15C:
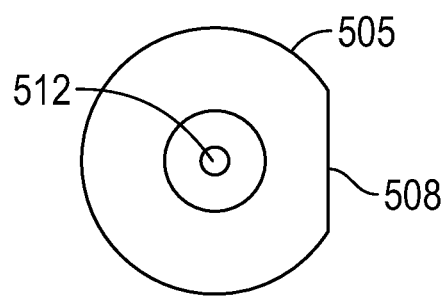

Referring now to FIGS. 15A-15O, shown therein is an embodiment of a testing device 500 and reader 501. The testing device 500 can be used for testing blood, or other sample(s) that would benefit from separating two constituent components in the sample. The testing device 500 will be described hereinafter by way of example as a blood testing device. The blood testing device 500 has a fluid housing 502, a fluid treatment module 503, a fluid reservoir 504 fluidly connected to the fluid treatment module 503. The fluid treatment module 503 includes a fluid treatment housing 505, an optical zone 506, a treatment window 508, and a flow port 512 within the fluid treatment housing 505. When the fluid treatment housing 505 of the fluid treatment module 503 is connected to the fluid housing 502, the fluid reservoir 504 is in fluid communication with the flow port 512 such that a sample within the fluid reservoir 504 can be directed to a treatment area 513 via the flow port 512. In one embodiment, the fluid housing 502 includes a syringe having a fluid fitting connected to the fluid treatment housing 505 of the fluid treatment module 503.

The reader 501 has a reading device 510 adjacent to the flow path 512 when the fluid treatment module 503 and the fluid housing 502 are positioned within a bay 531*a*, and an analysis unit 514. In this embodiment of the blood testing device 500, a blood sample is contained in the fluid housing 502 and directed along the flow path 512 into the fluid treatment area 513 where the blood sample is directed to flow past the treatment window 508. The treatment window 508 is constructed of a material that functions to pass acoustic forces generated by an acoustic transducer into the blood sample contained within the fluid housing 502.

The reading device 510 is part of the analysis unit 514 and is provided with an acoustic transducer (not shown) and an optical reader (not shown) which operate as described above to acoustically treat the blood sample. The acoustic transducer may be provided with a planar shape so as to mate with the treatment window 508 of the blood testing device 500. The optical reader of the reading device 510 has a field of view directed to the optical zone 506 where the acoustically treated blood sample may be read. The analysis unit 514 actuates the acoustic transducer to acoustically treat the blood sample and move the blood cells away from the optical zone 506 such that only the plasma is visible in the optical zone 506. Then the optical reader captures an image of the plasma and any backdrop and sends the image to the analysis unit 514 for colorimetric analysis as discussed above. The analysis unit 514 may be provided with further blood analysis features (not shown) such as blood gas analysis which may further analyze the blood sample after it passes through the flow path 512. The reader 501 may be portable and have a housing 518 that includes a slot 520 sized and dimensioned to receive the blood testing device 500 such that the optical zone 506 is in the field of view of the optical reader and the treatment window overlaps with the acoustic transducer. The housing 518 can be provided in a variety of shapes such as in a shape of a hot dog bun, for instance. The analysis unit 514 can be supported in the housing 518 or be separate therefrom. For example, the reading device 510 can be provided with a wireless transceiver to communicate with the analysis unit 514. The analysis unit 514 may be constructed and function in a similar manner as the control unit 460 discussed above.

Figure 16B:
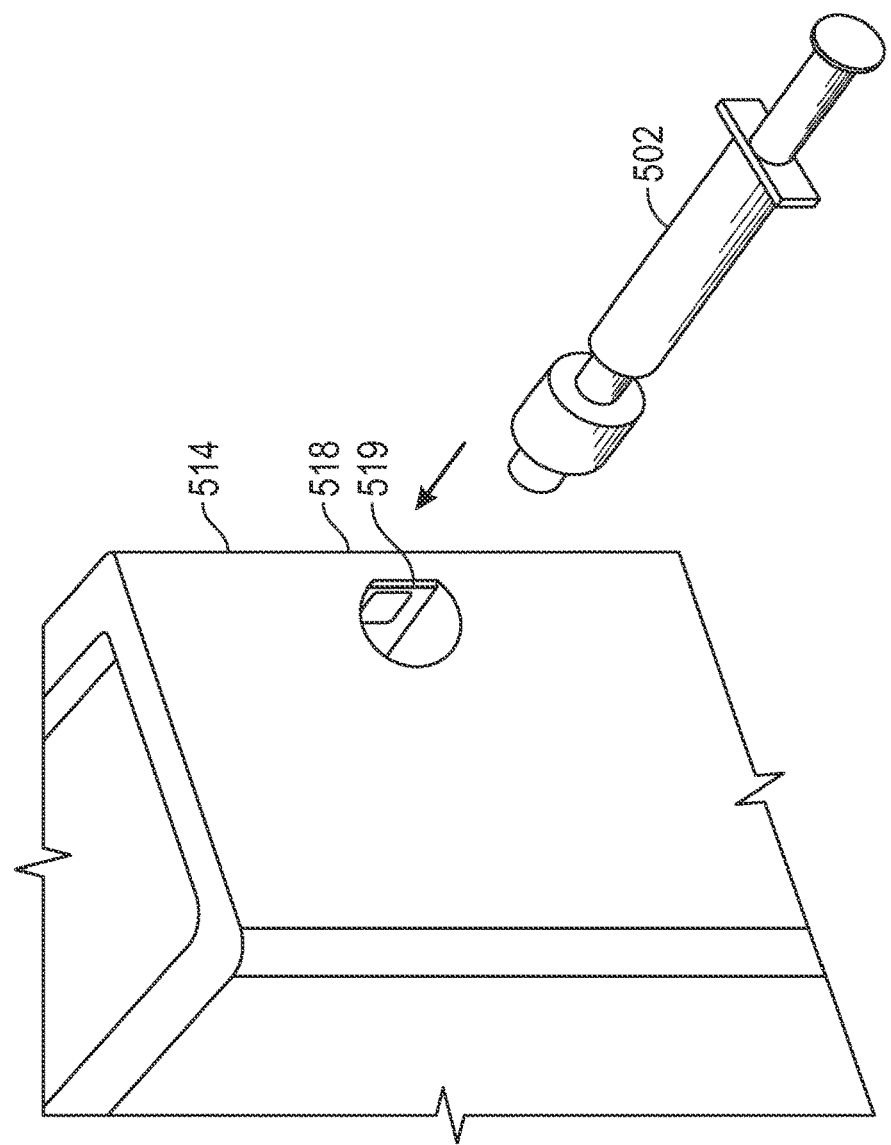
FIGS. 16A and 16B illustrate a fluid housing of FIG. 15A being inserted into an analysis unit for active separation in accordance with one embodiment of the present disclosure.
Figure 16A:
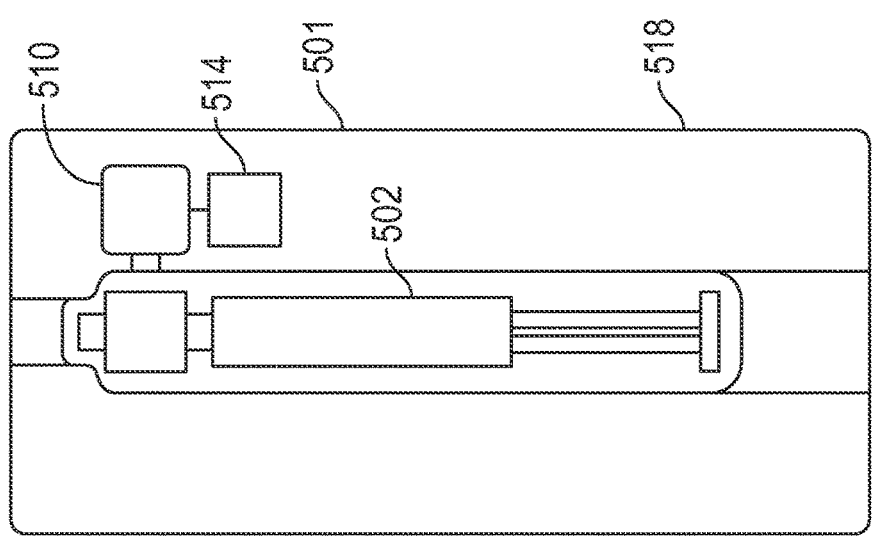

FIGS. 16A and 16B illustrate another variation of the reader 501 having a portion 519 in which the fluid treatment module 503 of FIG. 15A may be inserted into the housing 518 so that the blood sample, for example, may be acoustically treated and read by the reading device 510 within the housing 518 as described above. The portion 519 may be sized and adapted to mating receive the fluid treatment module 503 when the fluid treatment module 503 is connected to the fluid housing 502.

Referring now to FIGS. 17-19, shown therein is yet another version of a testing device 600 similar to the testing device 500 shown in FIG. 15A that can be read by the reader 501. The testing device 600 can be used for testing blood, or other sample(s) that would benefit from separating two constituent components in the sample. The testing device 600 will be described hereinafter by way of example as a blood testing device. In the interest of brevity, only the differences will be described in detail herein. The blood testing device 600 is provided with a fluid housing 602, a fluid treatment module 603, a fluid reservoir 604, and a fluid treatment housing 605. The fluid treatment housing 605 includes an optical zone 606, a treatment window 608, a flow path 612, a gate 614 having a port 616, and a gate guide channel 618.

When the gate 614 is in a first position (shown in FIG. 18), the flow path 612 is restricted such that a blood sample in the flow path 612 stops in the optical zone 606 where the sample may be acoustically treated to move undamaged blood cells away from the plasma adjacent to the optical zone 606 and read with the reader 501 as described above.

Once the blood sample has been analyzed the gate 614 may be moved to a second position (shown in FIG. 19), which moves the port 616 into the flow path 612 allowing the blood sample to pass.

Figure 22:
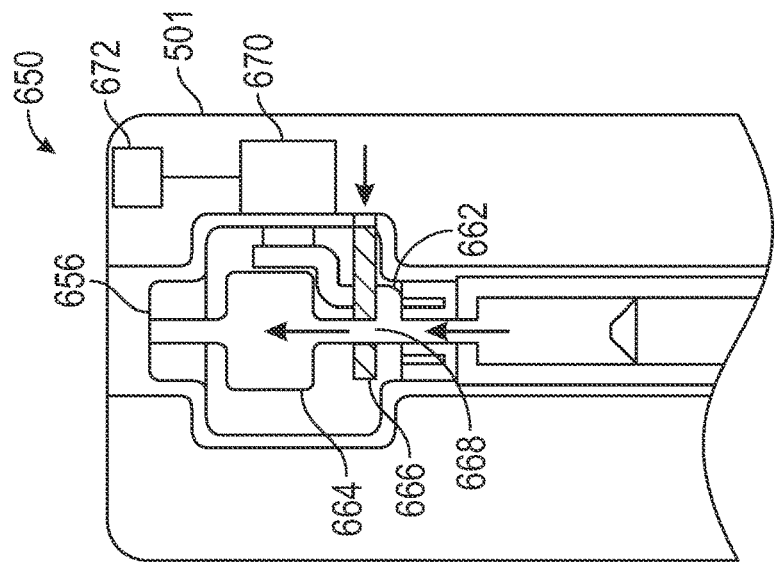
FIG. 22 illustrates the blood testing device of FIG. 14 having the moveable gate in a second position.
Figure 21:
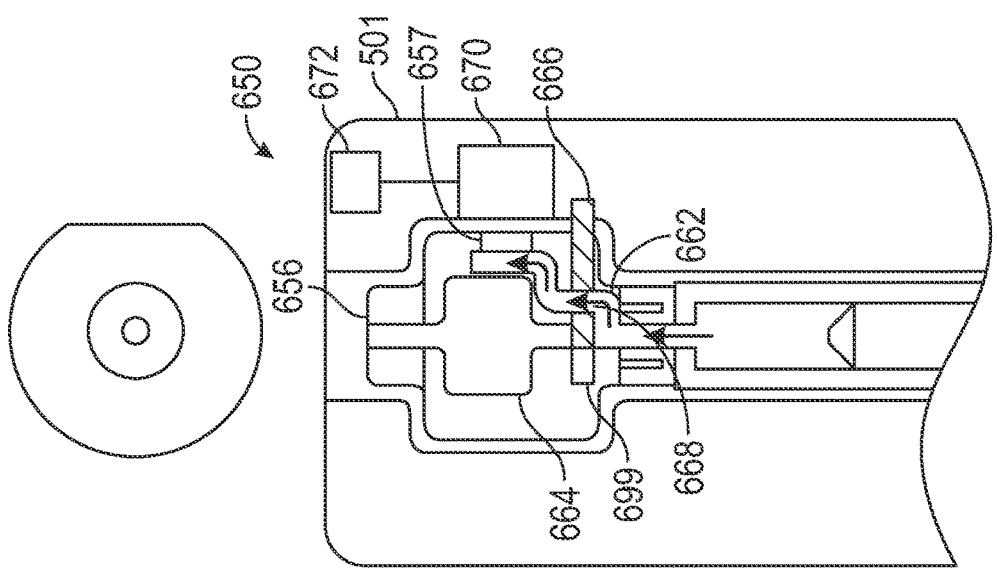
FIG. 21 illustrates the blood testing device of FIG. 14 having the moveable gate in a first position.
Figure 20:
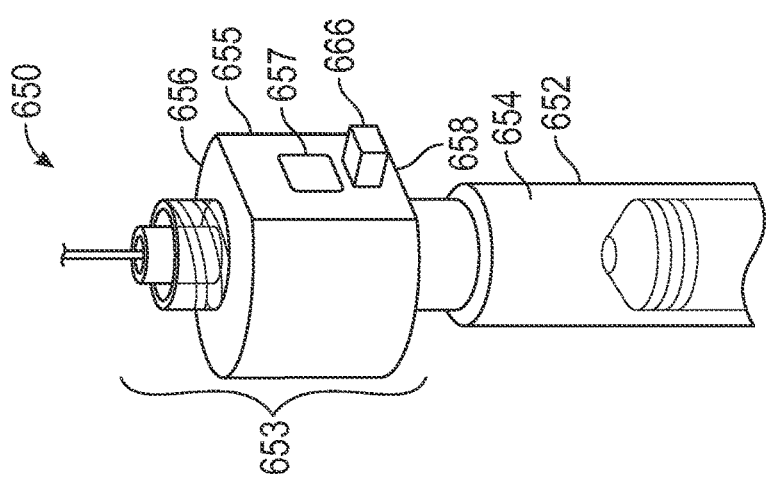
FIG. 20 illustrates a perspective view of a blood testing device having a moveable gate constructed in accordance with one embodiment of the present disclosure.

Referring now to FIGS. 20-22, shown therein is yet another version of a testing device 650 similar to the testing devices 500 and 600 shown in FIGS. 15A and 17-19, respectively, that can be read by the reader 501. In the interest of brevity, only the differences will be described in detail herein. The testing device 650 can be used for testing blood, or other sample(s) that would benefit from separating two constituent components in the sample. The testing device 650 will be described hereinafter by way of example as a blood testing device. The blood testing device 650 is provided with a fluid housing 652, a fluid treatment module 653, a fluid reservoir 654, and a fluid treatment module 655 connected to the fluid housing 652. The fluid treatment module 655 includes a fluid treatment housing 656. The fluid treatment housing 656 includes an optical zone 657, a treatment window 658, a first flow path 662, a second flow path 664. The fluid treatment module 655 includes a gate 666 having a port 668 positioned within a gate guide channel 699 of the fluid treatment housing 656.

When the gate 666 is in a first position (shown in FIG. 21), a blood sample is directed from the fluid housing 652 into the first flow path 662 such that the blood sample stops in the optical zone 657 where the blood sample may be acoustically treated with acoustic transducer 670 and read with the reading device 672 as described above.

Once the blood sample has been analyzed the gate 666 may be moved to a second position (shown in FIG. 22), which moves the port 668 into the second flow path 664 allowing the blood sample to pass through the second flow path 664.

Figure 23:
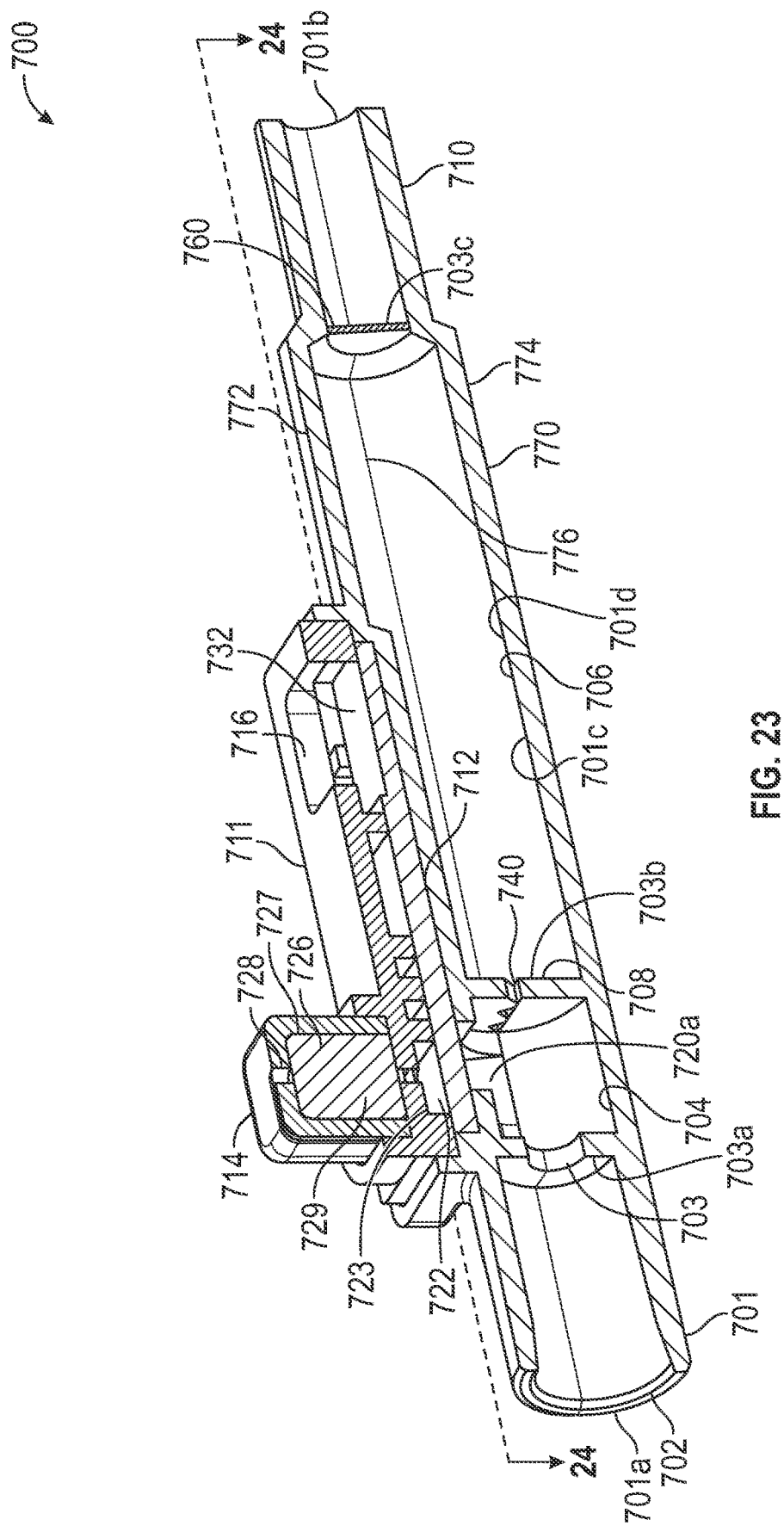
FIG. 23 illustrates a side, perspective cut away view of a fluid testing device having an air vent constructed in accordance with one embodiment of the present disclosure.
Figure 24:
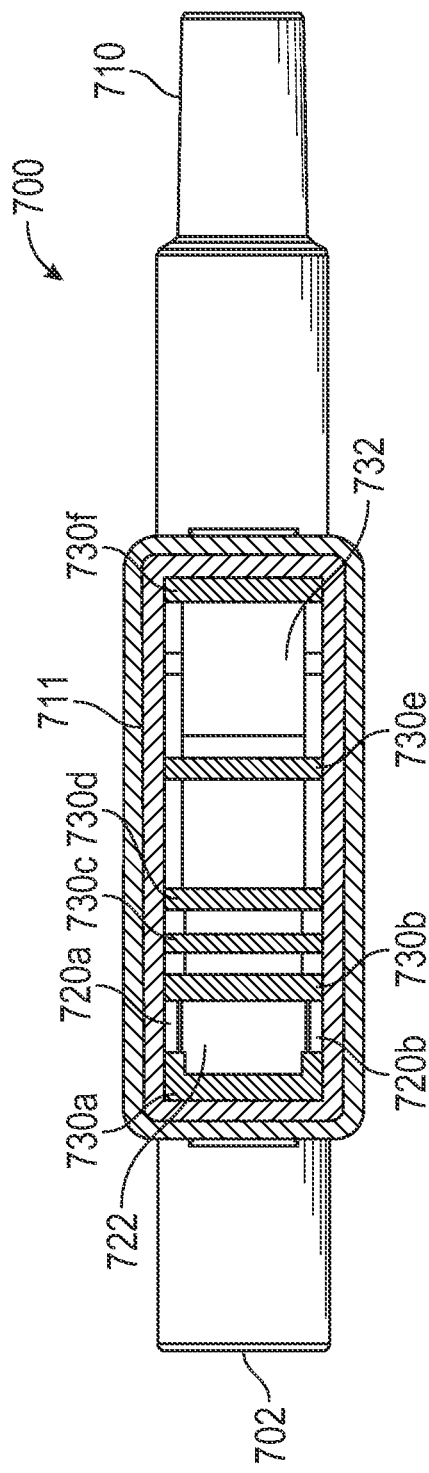
FIG. 24 illustrates a partial cut away top view of the fluid testing device of FIG. 23.
Figure 25:
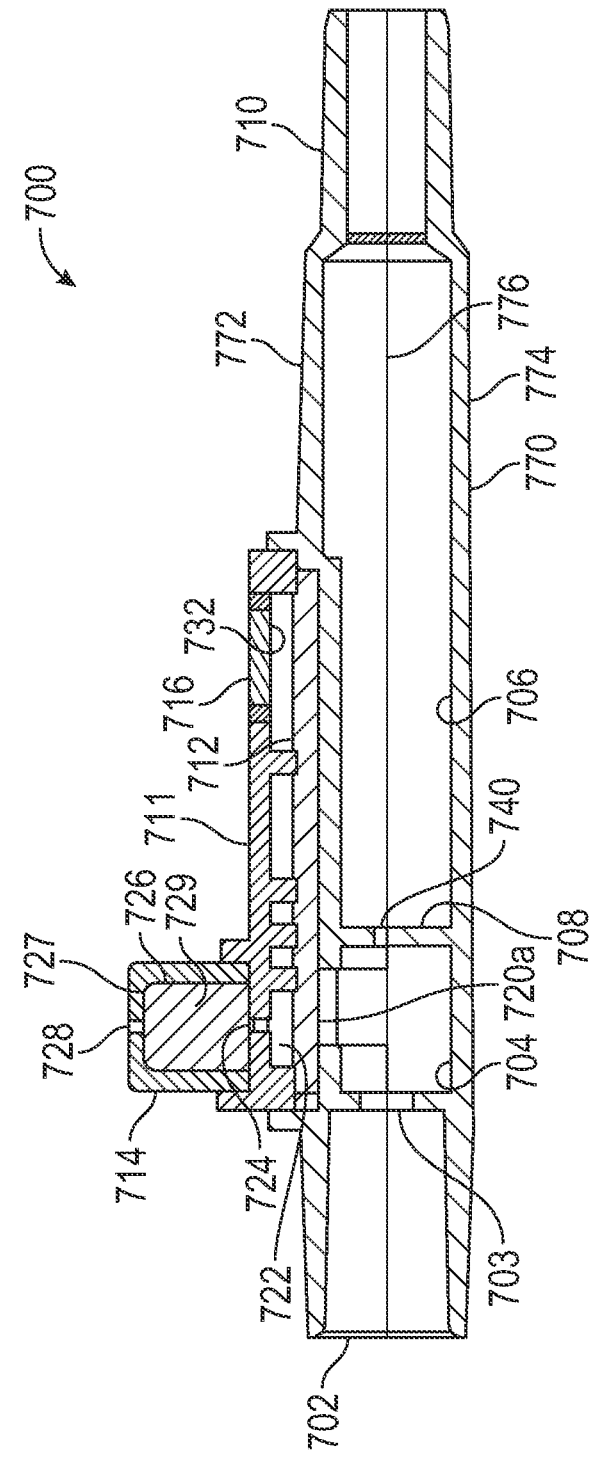
FIG. 25 is a cross-sectional view of the fluid testing device of FIG. 24, taken along the lines 25-25.

Referring now to FIGS. 23-25, shown therein is a fluid testing device 700 which may be removably attachable to a fluid collection device or a fluid housing such as a syringe, for example. The fluid testing device 700 may be provided with a tubular housing 701 having a first end 701a, a second end 701b, a bore 701c extending between the first end 701a and the second end 701b, and an interior surface 701d. The fluid testing device 700 is also provided with a connector 702 which may be located at the first end 701a. The fluid testing device 700 may also be provided with a first wall 703a, a second wall 703b, and a third wall 703c positioned within and extending across the bore 701c of the tubular housing 701. The first wall 703a, the second wall 703b, and the third wall 703c are spatially disposed between the first end 701a and the second end 701b of the tubular housing 701. As shown in FIG. 23, an aperture 703 extends through the first wall 703a so as to permit the sample to travel from the connector 702 past the first wall 703a. The first wall 703a, the second wall 703b, and the interior surface 701d of the tubular housing 701 between the first wall 703a and the second wall 703b define a first fluid chamber 704. The second wall 703b, the third wall 703c and the interior surface 701d between the second wall 703b and the third wall 703c define a second fluid chamber 706. A clot catcher 708 extends through the second wall 703b and connects the first fluid chamber 704 to the second fluid chamber 706. The third wall 703c and the interior surface 701d of the tubular housing 701 adjacent to the second end 701b define an outlet portion 710 of the tubular housing 701. As shown in FIG. 23, the fluid testing device 700 is also provided with a sensing housing 711 which may be connected to an exterior surface of the tubular housing 701. The sensing housing 711 encompasses and supports one or more lateral flow strip 712. A single lateral flow strip 712 is shown in FIG. 23 for purposes of brevity. The lateral flow strip 712 can be similar in construction and function as the lateral flow strip 112 discussed above. The sensing housing 711 also defines a vent portion 714, and an optical zone 716. In one embodiment, the lateral flow strip 712 is located outside of the tubular housing 701 and is positioned between the sensing housing 711 and the tubular housing 701.

The connector 702 may be provided with means for connecting the fluid testing device 700 to a syringe, for example, such as a screw coupling, a bayonet joint, or a snap lock coupling on the inside or the outside of the connector 702. For example, in one embodiment, the connector 702 may form a standard syringe luer for creating a leak-free connection between the fluid testing device 700 and a syringe (not shown). It should be understood, however, that the connector 702 may be any type of connector known in the industry for creating a leak-free connection between the blood testing device and a fluid sample container such as a syringe or fluid collection tube (commonly referred to as a vacutainer), for example.

The vent portion 714 allows equilibration of any pressure differences created during collection of test samples (e.g., air collected in a syringe), and thus allows gas to escape from the first fluid chamber 704. Gases may pass around the lateral flow strip 712 through at least one aperture 720a and 720b (see FIG. 24) formed in the tubular housing 701 into a separation chamber 722 defined by one or more walls 723 in the sensing housing 711. The apertures 720a and 720b may communicate with the first fluid chamber 704 and the separation chamber 722. The separation chamber 722 may also be defined by a portion of the lateral flow strip 712. As shown in FIG. 23, the separation chamber 722 is above the lateral flow strip 712.

In use, the connector 702 is attached to the syringe to form a fluid tight seal, and a sample is introduced into the first fluid chamber 704 from the syringe thereby forming a contained system where the sample is unlikely to leak from the fluid testing device 700. The third wall 703c may be a fluid impermeable/gas permeable membrane. In this instance, the sample also flows through the clot catcher 708 and into the second chamber 706. Any gas within the first chamber 704 is displaced by the sample into the aperture 720a and 720b and is vented through the vent portion 714. Any gas within the second chamber 706 is also displaced by the sample and vented through the third wall 703c. As the gas is displaced, pressure builds within the first chamber 704 and the second chamber 706 causing the sample to flow through the first and second apertures 720a and 720b into the separation chamber 722. Because the separation chamber 722 is bounded by the lateral flow strip 712, at least a portion of the sample is introduced into the lateral flow strip 712. Once the sample is introduced into the lateral flow strip 712, capillary action causes the sample to move within the lateral flow strip 712 toward the optical zone 716. When the sample is blood, as the sample moves through the lateral flow strip 712, the lateral flow strip may separate any blood cells from plasma prior to the plasma reaching the optical zone 716. The optical zone 716 can be a portion of the sensing housing 711 that can pass light within a visible part of the electromagnetic spectrum, thus permitting viewing of the plasma within the optical zone 716 to determine the results of one or more tests being conducted by the lateral flow strip 712. If the tests indicate that the sample should be subject to further testing, then the fluid sample may be transferred through the outlet portion 710 into a testing instrument, such as a blood gas analyzer or other suitable testing instrument for additional testing. Suitable testing instruments may include urine analyzers, blood analyzers, or the like. In certain cases, a pipette (also known as a "probe") (not shown) may be introduced through the outlet portion 710 and through the membrane 760 to draw a de-aerated sample from within the second fluid chamber 706. Once the testing instrument has the sample, then one or more further tests can be conducted on the sample by the testing instrument.

The gases may then pass through a first vent aperture 724 formed within the wall 723, and into a gas chamber 726 also defined by one or more walls 727 of the vent portion 714. The gases may then pass through the gas chamber 726 of the vent portion 714 and out through an optional second vent aperture 728 formed within the wall 727. The wall 727 can be cup shaped so as to define the gas chamber 726. The gas chamber 726 of the vent portion 714 may be filled with an absorbent material 729 that allows gas to pass through the absorbent material 729 while absorbing any fluid of the sample that may have entered the gas chamber 726 and passed through the first vent aperture 724.

The sensing housing 711 may also include a plurality of ribs 730a-f forming a tortuous path for the sample to flow between the first fluid chamber 704 and an optical chamber 732 to be viewed through the optical zone 716. The optical chamber 732 can be defined between the sensing housing 711 and the lateral flow strip 712. The ribs 730a-f engage the lateral flow strip 712 and define voids between the sensing housing 711 and the lateral flow strip 712. Any excess fluid of the sample flowing through the lateral flow strip 712 may be displaced into the voids so as to prevent oversaturation of the lateral flow strip 712 prior to the optical zone 716.

The ribs 730a-f help prevent leaking as well as assisting in the separation of fluid constituents such as red blood cells and plasma, for instance. Thus, when a fluid such as blood containing blood cells suspended within plasma is introduced into the fluid testing device 700, the red blood cells and plasma will be separated by the lateral flow strip 712 and the plasma will be visible in the optical chamber 732 through the optical zone 716 while the red blood cells remain in the first fluid chamber 704, the second fluid chamber 706, the separation chamber 722, the adsorbent material 729, and a portion of the lateral flow strip 712 used to separate the red blood cells from the plasma.

Under a predetermined amount of pressure, fluid may pass from the first fluid chamber 704 to the second fluid chamber 706 through the clot catcher 708. The clot catcher 708 may be provided with a plurality of apertures 740 (only one of which is numbered) which have a geometry and size designed to allow certain fluid constituents to pass through the second wall 703b while trapping larger constituents. For instance, when the fluid is blood containing red blood cells, plasma, and clotted blood, the clot catcher 708 will allow the plasma and the red blood cells to pass through into the second fluid chamber 706 while trapping the clotted blood in the first fluid chamber 704.

The outlet portion 710 is bounded by the third wall 703c, which may be in the form of a membrane 760 that closes the second fluid chamber 706 and keeps fluid from passing into the outlet portion 710 unless the membrane 760 is pierced. The membrane 760 may be formed of a fluid impermeable material. In some embodiments, the membrane 760 may be formed of a gas permeable but fluid impermeable material to allow any air that has entered the second fluid chamber 706 to pass through the membrane 760 and out through the outlet 710.

The outlet portion 710 may be sized and shaped to allow the fluid testing device 700 to be attached to a testing instrument such as a blood gas analyzer, for example. For instance, the outlet portion 710 of the fluid testing device 700 may form a standard syringe luer which provides a fluid tight seal with the testing instrument. Or, a probe or pipette from the testing instrument may be inserted through the outlet portion 710, through the membrane 760 to draw a sample from within the second fluid chamber 706.

In some embodiments of the fluid testing device 700, the tubular housing 701 may be constructed of a body 770 having a first piece 772 and a second piece 774 sealably connected along line 776. The sensing housing 711 may be formed of a separate component which is attached to the body 770. Likewise the wall 727 of the vent portion 714 may be constructed as a separate component that is then attached to the wall 723 of the sensing housing 711.

In some instances, the fluid testing device 700 can be made by forming the first piece 772, the second piece 774, the wall 723 and the wall 727. Then, the first piece 772 is connected to the second piece 774 to form the body 770. The lateral flow strip 712 is placed on a predetermined portion of the body 770, and then the wall 723 is connected to the body 770 to encapsulate the lateral flow strip 712. The absorbent material 729 is placed within the wall 727, and then the wall 727 is connected to the wall 723 as shown in FIG. 23 to encapsulate the absorbent material 729.

The tubular housing 701, the sensing housing 711, and the vent portion 714 may be formed of any appropriate material such as plastic, for instance. The tubular housing 701, the sensing housing 711, and the vent portion 714 may be formed using techniques such as injection molding, extrusion molding, vacuum casting, 3D printing, and the like. The tubular housing 701, the sensing housing 711, and the vent portion 714 may be joined using techniques and materials known in the art such as solvent bonding, heat, vibration welding, mechanical fastening, and the like.

In some embodiments of the fluid testing device 700, the first aperture 724 may include a gas permeable filter (not shown) designed to allow gas to pass through while keeping fluid in the separation chamber 722.

Figure 26:
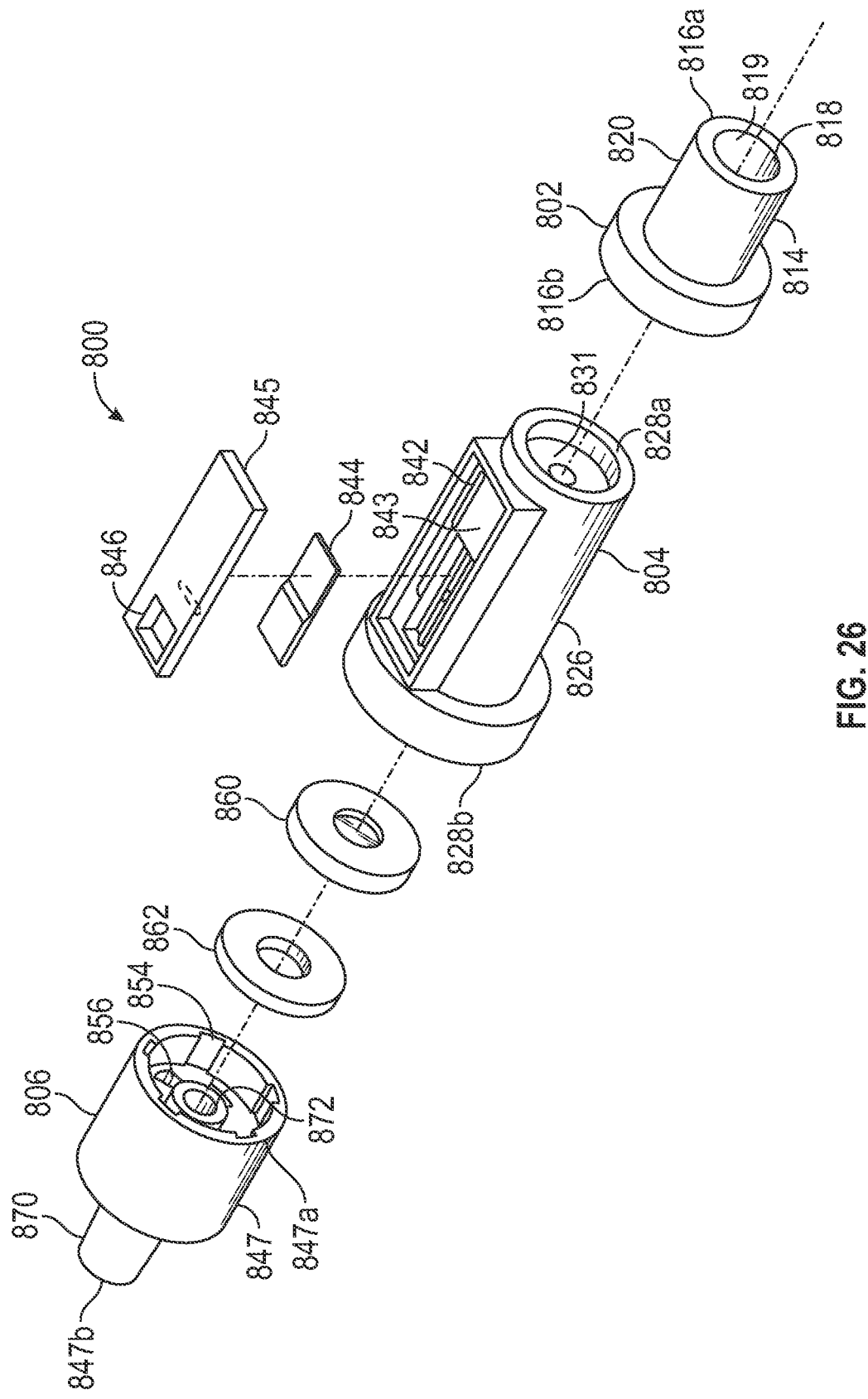
FIG. 26 illustrates an exploded view of a fluid testing device having an air vent constructed in accordance with one embodiment of the present disclosure.
Figure 27:
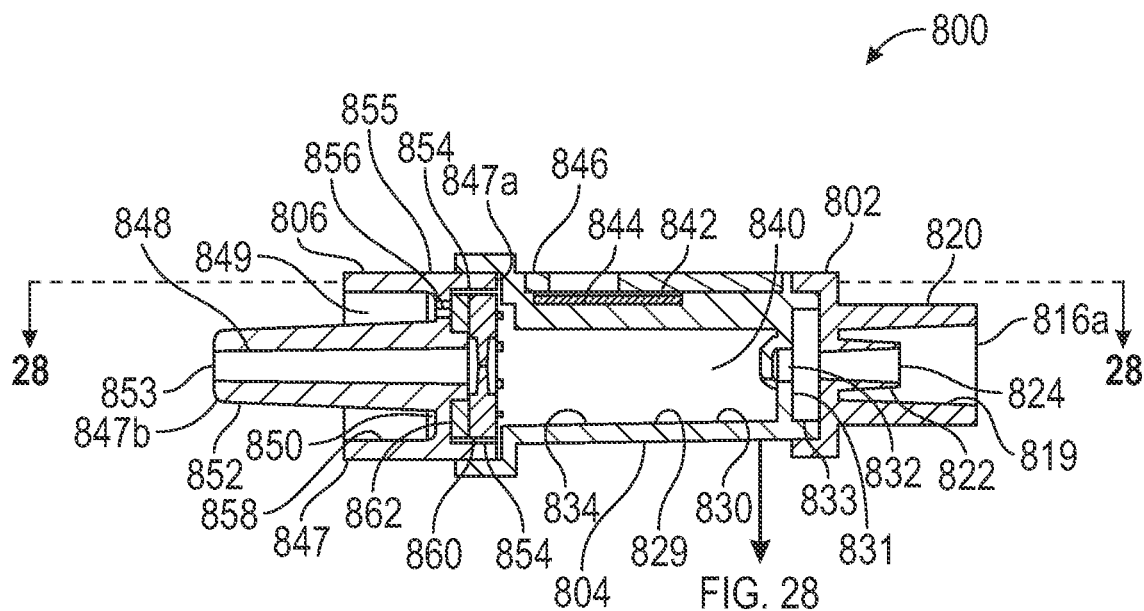
FIG. 27 illustrates an orthogonal cut away view of the fluid testing device of FIG. 26.
Figure 28:
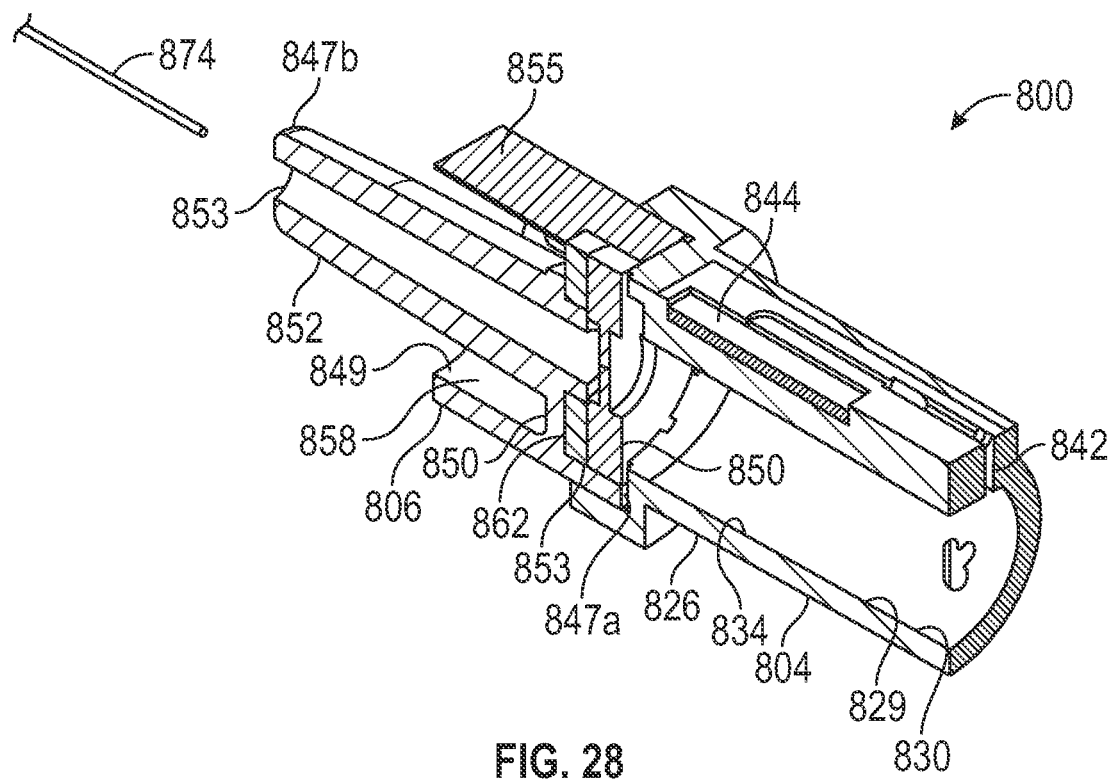
FIG. 28 illustrates a perspective cut away view of the fluid testing device of FIG. 27 taken along the lines 28-28 depicted in FIG. 27.
Figure 29:
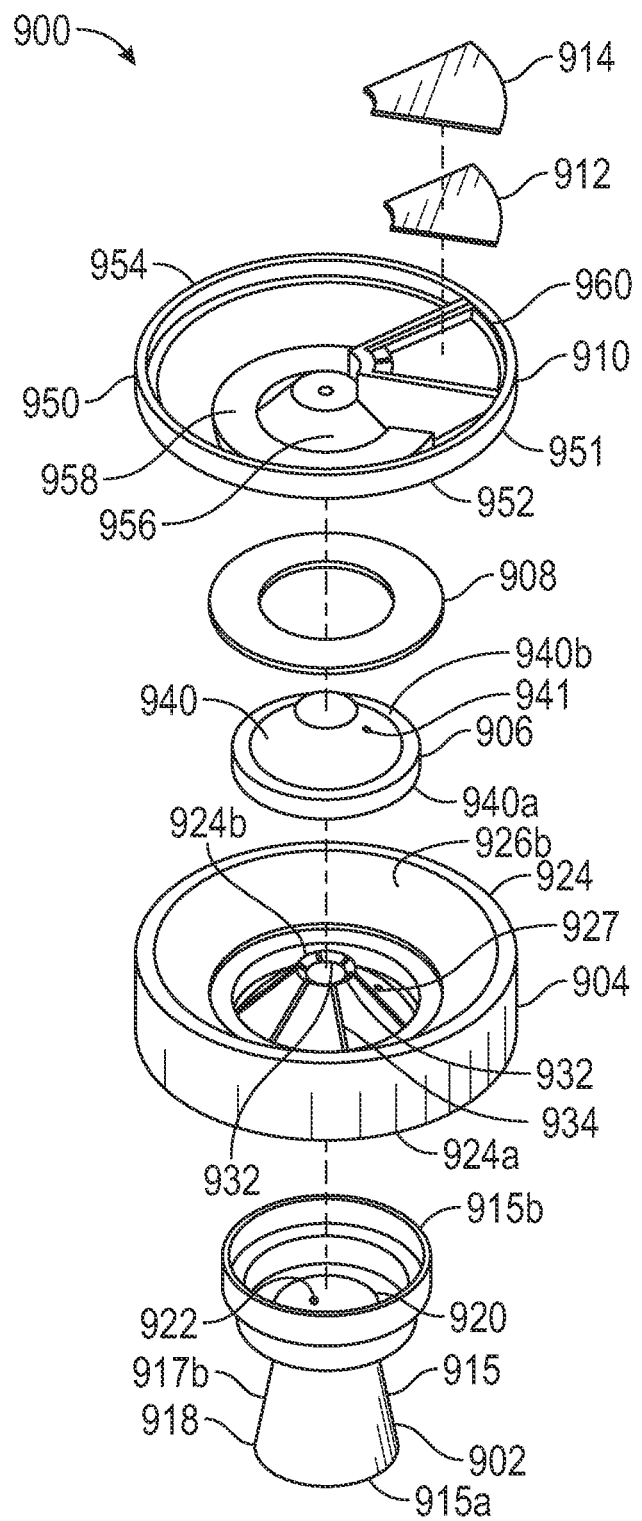
FIG. 29 illustrates an exploded view of a fluid testing device having an air vent constructed in accordance with one embodiment of the present disclosure.
Figure 30:
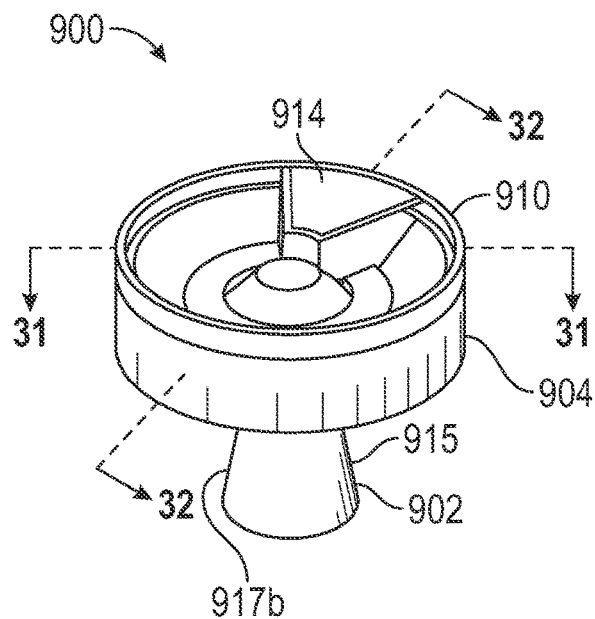
FIG. 30 illustrates a perspective view of the fluid testing device of FIG. 29.
Figure 31:
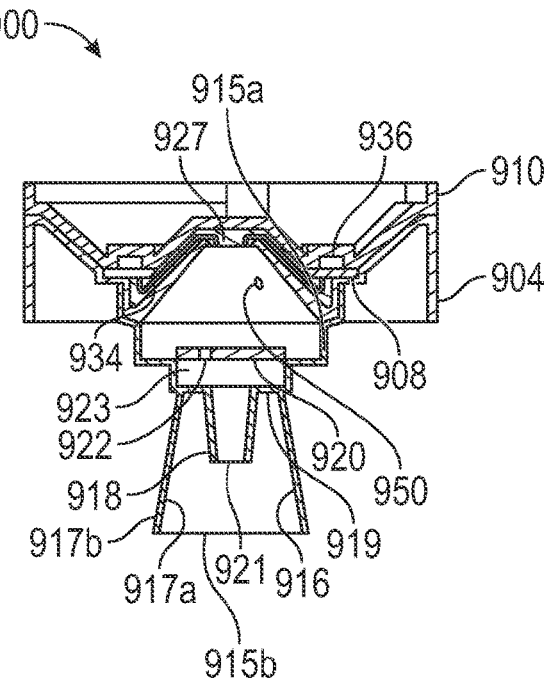
FIG. 31 illustrates an orthogonal cut away view of the fluid testing device of FIG. 29.
Figure 32:
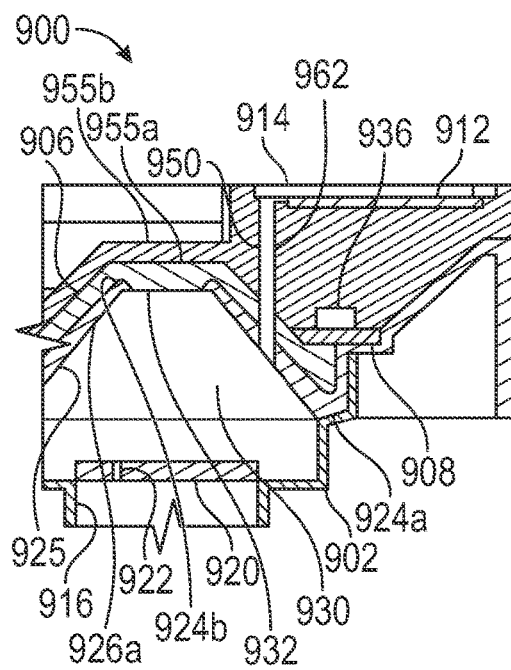
FIG. 32 illustrates a perspective cut away view of the fluid testing device of FIG. 29.

Referring now to FIGS. 26-28, a fluid testing device 800 is illustrated having an inlet portion 802, a container portion 804, and an outlet portion 806.

The inlet portion 802 may be sealably connected to the container portion 804 and the container portion 804 may be sealably connected to the outlet portion 806 using any known method in the industry. By way of example, the inlet portion 802, container portion 804, and outlet portion 806 may be connected using bonding agents such as glue or ultra-sonically welded, for instance.

The inlet portion 802 may be provided with a tubular housing 814 having a first end 816a, a second end 816b, a bore 818 extending from the first end 816a to the second end 816b, an interior surface 819, and a connector 820 located at the first end 816a. The inlet portion may also be provided with a first wall 822 positioned within and extending across the bore 818. As shown in FIG. 27, an aperture 824 extends through the first wall 822 so as to allow a sample to travel from the connector 820 through the first wall 822. The connector 820 may be any suitable type of connector, such as a Luer connector for connecting the fluid testing device 800 to a syringe, for instance, or other fluid containers.

The container portion 804 may be provided with a tubular housing 826 having a first end 828a, a second end 828b, a bore 829 extending from the first end 828a to the second end 828b, and an interior surface 830. The container portion 804 may also be provided with a second wall 831 positioned within and extending across the bore 818 and spatially disposed between the first end 828a and the second end 828b of the container portion 804. The second wall 831 and the interior surface 830 of the tubular housing 826 between the first end 828a and the second wall 831 define a first fluid chamber 833. A clot catcher 832 may extend through the second wall 831 and connects the inlet portion 802 to the first fluid chamber 833. The clot catcher 832 may operate as described above with regard to element 740. The interior surface 830 extending from the second wall 831 to the second end 828b define a second fluid chamber 834 of the container portion 804.

The fluid testing device 800 may also be provided with a sensing housing 845 having an optical zone 846. The sensing housing 845 may be connected to an exterior surface of the tubular housing 826 of the container portion 804. The sensing housing 845 encompasses and supports a test strip 844. In the illustrated embodiment, the test strip 844 is located outside of the tubular housing 826 and is positioned between the sensing housing 845 and the tubular housing 826.

A fluid channel 842 is formed in the tubular housing 826 between the interior surface 830 and a test chamber 843 defined between an exterior surface of the tubular housing 826 and an interior surface of the sensing housing 845. The test strip 844 may be positioned within the test chamber 843. When a fluid sample is introduced into the second fluid chamber 834, capillary action causes the sample to move through the fluid channel 842 and onto the test strip 844. The sample being on the test strip 844 can be observed through the optical zone 846. The test strip 844 may include one or more reagent which can react with the sample and be used to determine any number of conditions, such as blood type, pathological analysis, glucose levels, pregnancy, etc.

The outlet portion 806 may be provided with a tubular housing 847 having a first end 847a, a second end 847b, a bore 848 extending from the first end 847a to the second end 847b, an interior surface 849, a third wall 850, a connector 852, an outlet aperture 853 that passes through the third wall 850, at least one channel 854 formed in the interior surface 849, a shroud 855 extending circumferentially around the connector 852 and at least one air outlet aperture 856 that passes through the third wall 850. The third wall 850 is connected to and extends from the connector 852. In the example shown, the third wall 850 has a ring shape and extends around the connector 852. The shroud 855 is connected to the third wall 850 and extends around at least a portion of the connector 852. The shroud 855 is spaced a distance from the connector 852 to form a recess 858. The air outlet aperture 856 communicates with the recess 858 so that air passing through the air outlet aperture 856 from the channel 854 is exhausted into the recess 858.

A septum 860 and a filter 862 may be positioned within the outlet portion 806, generally at the first end 847a thereof. The septum 860 extends across the bore 848 so as to prevent gas or fluid from flowing through the bore 848. As shown in FIG. 27, the filter 862 is located downstream from the septum 860. The septum 860 may be located at the intersection of the second end 828b of the container portion 804 and the first end 847a of the outlet portion 806. The filter 862 extends across and covers the at least one air channel 854. The at least one air channel 854 (only one of which is numbered in FIG. 26) allows air to pass around the septum 860, through the filter 862, and out the air outlet aperture 856 without the air passing through the bore 848 defined by the connector 852. The filter 862 is constructed of a gas permeable, fluid impermeable material that allows passage of air, but prevents passage of fluid. Thus, any air in a fluid in the second fluid cavity 840 may pass through the air channel 854, around the septum 860, through the filter 862 and out of the outlet portion 806 through the air outlet 876. With respect to fluids, however, the septum 860 blocks the bore 848 to prevent fluids to pass into the bore 848, and the filter 862 blocks fluids from passing into the air channel 854.

The connector 852 of the outlet portion 806 may be sized and shaped to allow the fluid testing device 800 to be attached to testing instrument, such as a blood gas analyzer (not shown). For instance, the connector 852 of the outlet portion 806 may form a standard syringe Luer having an aperture 853 that allows a probe 874 of the testing instrument, such as a blood gas analyzer to pass through the bore 848 and into the second fluid cavity 840 by piercing the septum 860. The outlet portion 806 and the container portion 804 of the fluid testing device 800 may be sized such that the probe 874 of the testing instrument does not pass through the container portion 804 but draws fluid to be tested from the second fluid cavity 840.

In use, when the fluid container is attached to the fluid testing device 800 and a sample is introduced into the first fluid cavity 833, any gas within the fluid container and the first fluid cavity are displaced by the sample through the clot catcher 832 and into the second fluid cavity 840 in the container portion 804. The clot catcher 832 may operate as described above with regard to element 740. Any gas within the second chamber is also displaced by the sample and vented through the air outlet 856 of the third wall 850 into the recess 858. The sample may pass by capillary action from the second fluid cavity 840 through fluid channel 842 onto the test strip 844. The test strip 844 may be observed through optical zone 846.

Referring now to FIGS. 29-32, a fluid testing device 900 is shown. The fluid testing device 900 may be provided with an inlet portion 902, a body portion 904, a fluid director 906, a filter 908, a cap 910, a test strip 912, and an optical zone 914.

The inlet portion 902 may be provided with a housing 915 having a first end 915a, a second end 915b, a bore 916 extending between the first end 915a and the second end 915b, an interior surface 917a, and an exterior surface 917b. The inlet portion 902 may also be provided with a connector 918 located at the first end 915a and extending into the bore 916. The connector 918 may be any suitable type of connector, such as a Luer connector for connecting the fluid testing device 900 to a syringe (not shown), for instance, or other fluid containers or testing devices.

The inlet portion 902 may further be provided with a first wall 919 positioned within and extending across the bore 916. The first wall 919 connects the housing 915 to the connector 918. As shown, the first wall 919 may have a ring shape. An aperture 921 extends through the connector 918 and the first wall 919. The inlet portion 902 may further be provided with a clot catcher 920 disposed within the bore 916 of the inlet portion 902. The clot catcher 920 may be downstream of the connector 918, and extend across the bore 916 so as to form a first fluid cavity 923 downstream of the connector 918. The first fluid cavity 923 is defined by the clot catcher 920, the first wall 919, and the housing 915. The clot catcher 920 may be provided with a plurality of apertures 922 (only one of which is numbered in FIG. 29) which are sized and shaped as has been described herein to allow fluid to pass through but catch fluid constituents that are larger than a predetermined size.

The body portion 904 may be provided with a housing 924 having a first end 924a, a second end 924b, a bore 925 extending between the first end 924a and the second end 924b, an interior surface 926a, an exterior surface 926b, and an aperture 927 extending between the interior surface 926a and the exterior surface 926b.

The body portion 904 may be connected to the inlet portion 902 with a portion of the bore 925 of the body portion 904 and a portion of the bore 916 of the inlet portion 902 forming a second fluid cavity 930. The body portion 904 may be further provided with an outlet 932 extending between the interior surface 926a and the second end 924b and a plurality of air channels 934 (only one of which is numbered in FIG. 29) formed in the exterior surface 926b that direct fluid and air from the second fluid cavity 930 to the filter 908 as will be explained in further detail herein. The filter 908 may be a gas permeable/fluid impermeable material that allows the air to pass through while preventing the fluid from passing thus venting any air in the fluid. In some embodiments, an air channel 936 may be formed in a shoulder 968 of the cap 910 which supports and engages a portion of the filter 908 and allows air to pass through the filter 908 into the air channel 936 as will be explained in further detail herein.

The fluid director 906 may be provided with a conical body 940 having an interior surface 940a and an exterior surface 940b and an aperture 941 extending between the interior surface 940a and the exterior surface 940b. The conical body 940 may be provided with a frusto-conical shape. The fluid director 906 may be sized and shaped such that at least a portion of the interior surface 940a of the fluid director 906 engages at least a portion of the exterior surface 926b of the body portion 904. When the fluid director 906 and the body portion 904 are connected, the aperture 941 of the fluid director 906 and the aperture 927 of the body portion 904 are aligned.

The cap 910 may be provided with a housing 951 having a first end 952, a second end 954, an interior surface 955a, an exterior surface 955b, a frusto-conically shaped center portion 956, the shoulder portion 958, a testing portion 960 sized and shaped to encompass and support the test strip 912, and an aperture 962 extending between the interior surface 955a and the testing portion 960.

The conically shaped center portion 956 may be sized and shaped such that at least a portion of the interior surface 955a of the cap 910 engages at least a portion of the exterior surface 940b of the fluid director 906. When the cap 910 is connected to the body portion 904 and the fluid director 906, apertures 927, 941, and 962 are aligned to form a passage 950.

In use, the connector 918 of the fluid testing device 900 may be connected to the syringe and a sample is introduced through the aperture 921 into the first fluid cavity 923. Fluid and any gas introduced into the first fluid cavity 923 of the fluid testing device 900 pass through the clot catcher 920 and enter the second fluid cavity 930 where the fluid may be tested. Any gas within the second fluid cavity 930 and any air introduced into the second fluid cavity 930 from the syringe are displaced and pass through channels 934 and are vented through filter 908. As the gas is displaced, pressure builds in the second fluid cavity 930 and at least a portion of the sample may travel through passage 950 and flow onto the test strip 912 which can be viewed through the optical zone 914. The fluid may move through the passage 950 under pressure, or, the fluid may move through the passage 950 by capillary action. The test strip 912 may be any type of test strip for testing fluid.

Figure 33:
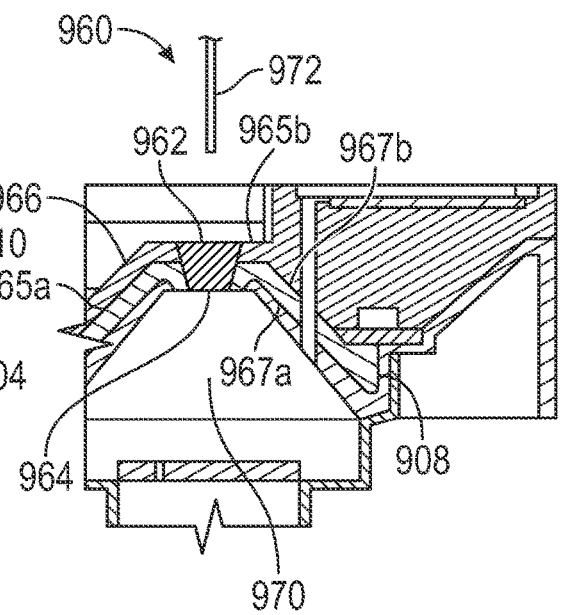
FIG. 33 illustrates an orthogonal cut away view of a fluid testing device having a pierceable membrane constructed in accordance with one embodiment of the present disclosure.

Referring now to FIG. 33, a fluid testing device 960 is shown. The fluid testing device 960 is similar to the fluid testing device 900 described above, therefore, in the interest of brevity only the differences will be described herein. The fluid testing device may be provided with a membrane 962 that seals an aperture 964 that is formed between an interior surface 965a and an exterior surface 965b of a cap 966 and an interior surface 967a and an exterior surface 967b of a fluid director 968 allowing access to a fluid cavity 970. For instance, the membrane 962 of the fluid testing device 960 may be penetrated by a probe 972 to withdraw fluid from the fluid cavity 970. As described above, the probe 972 may be part of a testing instrument such as a blood gas analyzer (not shown), and the fluid testing device 960 may be sized to ensure that the probe 972 stays in the fluid cavity 970 when fully inserted such that fluid is drawn from the fluid cavity 970 by the blood gas analyzer.

The following is a number list of non-limiting illustrative embodiments of the inventive concept disclosed herein:

1. A device, comprising:
    a housing constructed of a fluid impermeable material, and defining a first fluid port, and a second fluid port, the first fluid port configured to connect to a fluid collection device to receive a fluid sample from the fluid collection device into the housing, and the second port configured to pass the fluid sample from the housing into a testing instrument;
    a zone formed in the housing, the zone constructed of a material that allows an analysis of the fluid sample positioned within the housing, and located adjacent to the zone; and
    means for testing the fluid sample within the housing.

2. The device of illustrative embodiment 1, wherein the means for testing the fluid sample within the housing includes a matrix supported by the housing and positioned adjacent to the zone such that the fluid sample passed from the first fluid port to the matrix is treated prior to entering the zone.

3. The device of any one of illustrative embodiments 1 or 2, wherein the housing is separate from the fluid collection device, and wherein the fluid collection device is a syringe.

4. The device of any one of illustrative embodiments 1-3, wherein the fluid collection device is a syringe, and the testing instrument is an analyzer.

5. The device of illustrative embodiment 4, wherein the analyzer is a blood gas analyzer.

6. The device of illustrative embodiment 2, wherein the fluid sample is blood having red blood cells and plasma, and wherein the matrix is configured to separate the red blood cells from the plasma to present plasma substantially devoid of red blood cells within the zone.

7. The device of any one of illustrative embodiments 1-6, wherein the zone is an optical zone and wherein the optical zone is constructed of a material that is transparent to visible light.

8. The device of illustrative embodiment 2, wherein the matrix is a lateral flow membrane.

9. The device of illustrative embodiment 8, wherein the matrix is devoid of treatment with a reagent.

10. The device of illustrative embodiment 8, wherein the housing has an upper portion, a lower portion and a side, and wherein the lateral flow membrane is situated on the side of the housing.

11. The device of illustrative embodiment 8, wherein the housing has an upper portion, a lower portion, and a longitudinal axis extending between the upper portion and the lower portion, and wherein the lateral flow membrane has a major axis extending in a non-parallel relationship with the longitudinal axis.

12. The device of illustrative embodiment 11, wherein the major axis extends side to side relative to the longitudinal axis.

13. The device of any one of illustrative embodiments 1-12, wherein the housing defines a first fluid reservoir, and wherein the housing defines a second fluid reservoir separated from the first fluid reservoir with a fluid impermeable divider, the housing having a fluid channel through the fluid impermeable divider connecting the first fluid reservoir and the second fluid reservoir, and wherein the matrix is positioned in the second fluid reservoir.

14. The device of illustrative embodiment 13, wherein the fluid channel is spaced a distance from the zone.

15. The device of any one of illustrative embodiments 1-14, further comprising a gas permeable/liquid impermeable membrane covering a third fluid port positioned between the first fluid port and the second fluid port.

16. The device of illustrative embodiment 2, wherein the matrix is a flow membrane configured to separate red blood cells from plasma.

17. The device of any one of illustrative embodiments 2 or 16, wherein the matrix is treated with a reagent.

18. The device of illustrative embodiment 2, wherein the fluid sample is blood having red blood cells and plasma, and wherein the matrix is configured to separate the red blood cells from the plasma to present plasma substantially devoid of red blood cells within the zone.

19. The device of illustrative embodiment 1, wherein the zone is an optical zone and wherein the optical zone is constructed of a material that is transparent to visible light.

20. The device of illustrative embodiment 2, wherein the matrix has a distal end in the zone, and wherein the distal end is treated with a reagent.

21. The device of illustrative embodiment 2, wherein the matrix has a proximal end away from the zone, and wherein the proximal end is treated with the reagent.

22. The device of any one of illustrative embodiments 1-21, wherein the first fluid port includes a needle.

23. The device of any one of illustrative embodiments 1-21, wherein the second fluid port is a luer connector.

24. The device of any one of illustrative embodiments 1-21, wherein the second fluid port is a male port.

25. The device of any one of illustrative embodiments 1-21, wherein the second fluid port is a female port.

26. A method comprising:
    extracting a fluid sample from a fluid source with a fluid collection device having a first fluid housing such that the fluid sample is positioned within a first fluid reservoir defined by the first fluid housing;
    connecting a first fluid housing to a second fluid housing;
    passing a portion of the fluid sample from the first fluid reservoir in the first fluid housing into a second fluid reservoir in the second fluid housing, at least a portion of the fluid sample interacting with at least one of a matrix and a sensor in the second fluid housing;
    analyzing the fluid sample in the second fluid housing to conduct a first test of the fluid sample;
    passing a portion of the fluid sample from the second fluid reservoir into an analyzer; and
    analyzing the fluid sample in the analyzer to conduct a second test of the fluid sample.

27. The method of illustrative embodiment 26, wherein the second fluid housing has a third fluid reservoir separated from the second fluid reservoir by a fluid impermeable divider, and wherein a least a portion of the fluid sample passes from the second fluid reservoir into the third fluid reservoir via a fluid channel through the fluid impermeable divider, the portion of the fluid sample interacting with the at least one sensor or matrix in the third fluid reservoir.

28. The method of illustrative embodiment 27, wherein the matrix is a flow membrane in the third fluid reservoir, and wherein the method comprises the flow membrane separating the portion of the fluid sample into at least two constituent parts.

29. The method of illustrative embodiment 28, wherein the fluid sample is blood, and wherein the at least two constituent parts includes red blood cells, and plasma.

30. The method of illustrative embodiment 28, wherein the sensor includes a reagent.

31. The method of any one of illustrative embodiments 26-29, wherein the sensor includes a reagent.

32. The method of illustrative embodiment 26, wherein the sensor is an electrochemical sensor.

33. The method of any one of illustrative embodiments 26-32, wherein the fluid collection device is a syringe, and the fluid sample is a bodily fluid.

34. The method of any one of illustrative embodiments 26-32, wherein the fluid collection device is a vacutainer, and the fluid sample is a bodily fluid.

35. A method, comprising:
passing a fluid sample of blood containing blood cells and plasma from a syringe having a first fluid reservoir in a first fluid housing into a second fluid reservoir in a second fluid housing,
separating the blood cells from the plasma within the second fluid reservoir into a first zone containing plasma and blood cells, and a second zone containing plasma and being substantially devoid of blood cells;
analyzing the plasma within the second zone to determine a degree of hemolysis within the blood sample; and
passing a portion of the fluid sample containing red blood cells and plasma into an analyzer subsequent to analyzing the plasma within the second zone.

36. The method of illustrative embodiment 35, wherein the analyzer is a blood gas analyzer.

37. The method of any one of illustrative embodiments 35-36, wherein analyzing the plasma includes a colorimetric analysis of the plasma.

38. The method of any one of illustrative embodiments 35-36, wherein analyzing the plasma includes analyzing the plasma with a sensor.

39. The method of illustrative embodiment 38, wherein the sensor includes a reagent.

40. The method of illustrative embodiment 38, wherein the sensor is an electrochemical sensor.

41. The method of any one of illustrative embodiments 35-40, wherein separating the blood cells from the plasma within the second fluid reservoir into the first zone containing plasma and blood cells, and the second zone containing plasma and being substantially devoid of blood cells is defined further as separating the blood cells from the plasma by actuating a transducer to generate forces applied to the plasma and blood cells within the second fluid reservoir.

42. The method of illustrative embodiment 41, wherein the transducer is an acoustic transducer.

43. The method of illustrative embodiment 41, wherein the transducer is a magnetic transducer.

44. The method of illustrative embodiment 41, wherein the transducer is a dielectrophoretic transducer.

45. The method of any one of illustrative embodiments 41-44, wherein the transducer is located outside of the second fluid housing.

46. The method of any one of illustrative embodiments 41-45, wherein the second fluid housing has a port in communication with the second fluid reservoir, and further comprising passing at least a portion of the plasma that is substantially devoid of blood cells out of the second fluid reservoir through the port.

47. A fluid testing device, comprising:
a housing constructed of a fluid impermeable material and having a first fluid port configured to receive a fluid sample from a fluid collection device and a second fluid port configured to pass a portion of the fluid sample to an analyzer;
an optical zone formed in the housing, the optical zone constructed of a material that allows a colorimetric analysis of the fluid sample positioned within the housing, and located adjacent to the optical zone; and
a lateral flow membrane positioned between the housing and the optical zone such that a portion of the fluid sample to be received by the first fluid port from the fluid collection device passes through the lateral flow membrane to direct a portion of the fluid sample to enter the optical zone.

48. The fluid testing device of illustrative embodiment 47, further comprising a piston positioned within the housing.

49. An assembly, comprising:
a fluid collection device having a first fluid reservoir containing a fluid sample, the fluid sample being a bodily fluid;
a fluid treatment module comprising a housing having a first fluid port and a second fluid port, the first fluid port connected to the fluid collection device, the fluid treatment module defining a second fluid reservoir and a testing device within the housing, the testing device receiving a portion of the fluid sample and conducting a first test of the portion of the fluid sample; and
an analyzer connected to the second fluid port of the fluid treatment module when the first fluid port of the fluid treatment module is connected to the fluid collection device, the analyzer receiving a portion of the fluid sample from at least one of the fluid collection device and the fluid treatment module, the analyzer configured to conduct a second test of the portion of the fluid sample.

50. The assembly of illustrative embodiment 49, wherein the fluid collection device is a syringe.

51. The assembly of illustrative embodiment 49 or 50, wherein the testing device is a lateral flow membrane.

52. The assembly of illustrative embodiment 51, wherein the housing of the fluid treatment module has an upper portion, a lower portion and a side, and wherein the lateral flow membrane is situated on the side of the housing.

53. The assembly of illustrative embodiment 51, wherein the housing has an upper portion, a lower portion, and a longitudinal axis extending between the upper portion and the lower portion, and wherein the lateral flow membrane has a major axis extending in a non-parallel relationship with the longitudinal axis.

54. The assembly of illustrative embodiment 53, wherein the major axis extends side to side relative to the longitudinal axis.

55. The assembly of illustrative embodiment 49, wherein the housing of the fluid treatment module defines a third fluid reservoir separated from the second fluid reservoir with a fluid impermeable divider, the housing having a fluid channel through the fluid impermeable divider connecting the second fluid reservoir and the third fluid reservoir, and wherein the testing device is positioned in the third fluid reservoir.

56. The assembly of illustrative embodiment 55, wherein the fluid channel is spaced a distance from the zone.

57. The assembly of any one of illustrative embodiments 49-56, further comprising a gas permeable membrane positioned within the housing of the fluid treatment module, and wherein the analyzer includes a probe extending through the gas permeable membrane.

58. The assembly of illustrative embodiment 49, wherein the testing device is a flow membrane configured to separate red blood cells from plasma.

59. The assembly of illustrative embodiment 49, wherein the testing device includes a matrix treated with a reagent.

60. The assembly of any one of illustrative embodiments 49-59, wherein the first fluid port includes a needle.

61. The assembly of any one of illustrative embodiments 49-60, wherein the second fluid port is a luer connector.

62. The assembly of any one of illustrative embodiments 49-59, wherein the second fluid port is a male port.

63. The assembly of any one of illustrative embodiments 49-59, wherein the second fluid port is a female port.

64. A method, comprising:
receiving a bodily sample from a patient into a fluid collection device;
passing a first portion of the bodily sample from the fluid collection device into a fluid treatment module;
conducting a test on the bodily sample within the fluid treatment module; and
passing a second portion of the bodily sample through at least a portion of the fluid treatment module into an analyzer.

65. The method of illustrative embodiment 64, wherein the test is a first test, and further comprising conducting a second test on the second portion of the bodily sample within the analyzer.

66. The method of illustrative embodiment 65, wherein the first test is conducted prior to passing the second portion of the bodily sample into the analyzer.

67. The method of illustrative embodiment 64, wherein passing the second portion of the bodily sample into the analyzer is defined further as passing the second portion of the bodily sample through at least a portion of the fluid treatment module into the analyzer when the fluid treatment module is connected to the fluid collection device.

68. The method of any one of illustrative embodiments 64-67, wherein the fluid collection device is a syringe.

69. The method of any one of illustrative embodiments 64-67, wherein the fluid collection device is a vacutainer.

70. The method of any one of illustrative embodiments 64-67, wherein the fluid treatment module includes a housing defining a first fluid reservoir separated from a second fluid reservoir by a fluid impermeable divider, and wherein a least a portion of the bodily sample passes from the first fluid reservoir into the second fluid reservoir via a fluid channel through the fluid impermeable divider, the portion of the bodily sample interacting with at least one sensor or matrix in the second fluid reservoir.

71. The method of illustrative embodiment 70, wherein the matrix is a flow membrane in the second fluid reservoir, and wherein the method comprises the flow membrane separating the portion of the bodily sample into at least two constituent parts.

72. The method of illustrative embodiment 71, wherein the bodily sample is blood, and wherein the at least two constituent parts includes red blood cells and plasma.

73. The method of illustrative embodiment 70, wherein the sensor includes a reagent.

74. The method of illustrative embodiment 70, wherein the sensor is an electrochemical sensor.

75. The method of any one of illustrative embodiments 64-74, wherein passing the second portion of the bodily sample through at least a portion of the fluid treatment module into the analyzer includes inserting a probe from the analyzer into a fluid port of the fluid treatment module.

76. The method of illustrative embodiment 75, wherein the probe includes an end, and wherein inserting the probe from the analyzer into the fluid port of the fluid treatment module includes inserting the end of the probe through the fluid treatment module and into the fluid collection device.

77. The method of illustrative embodiment 75, wherein the probe includes an end, and wherein inserting the probe from the analyzer into the fluid port of the fluid treatment module includes inserting the end of the probe into the fluid treatment module without the end of the probe entering into the fluid collection device.

78. A fluid testing assembly, comprising:
a fluid testing device, comprising:
a housing constructed of a fluid impermeable material;
a treatment window formed in the housing, the treatment window constructed of a material capable of passing forces into the housing;
an optical zone formed in the treatment window of the housing, the optical zone constructed of a material that allows a colorimetric analysis of a fluid sample positioned within the housing, and located adjacent to the optical zone; and
a reader, comprising:
a bay for receiving at least a portion of the fluid testing device;
a transducer positioned adjacent to the bay such that when the fluid testing device is positioned within the bay, the transducer is configured to selectively generate forces directed through the treatment window of the housing and into the fluid sample; and
a control unit for selectively actuating and deactivating the transducer; and
a sensor positioned adjacent to the optical zone for obtaining colorimetric information from the optical zone.

79. The fluid testing assembly of illustrative embodiment 78, wherein the transducer is an acoustic transducer.

80. The fluid testing assembly of illustrative embodiment 78, wherein the transducer is a magnetic transducer.

81. The fluid testing assembly of illustrative embodiment 78, wherein the transducer is a dielectrophoretic transducer.

82. The fluid testing assembly of any one of illustrative embodiments 78-81, wherein the fluid sample has a first constituent part and a second constituent part, the housing defining a first channel and a second channel adjacent to the treatment window such that the first channel is positioned to receive the first constituent part and the second channel is positioned to receive the second constituent part.

83. The fluid testing assembly of any one of illustrative embodiments 78-82, wherein the housing includes an optical zone formed in the treatment window of the housing, the optical zone constructed of a material that allows the colorimetric analysis of the fluid sample, the fluid sample positioned within the housing and located adjacent to the optical zone.

84. The fluid testing assembly of any one of illustrative embodiments 78-83, wherein the fluid testing device is integrated with a fluid collection device.

85. The fluid testing assembly of illustrative embodiment 84, wherein the fluid collection device is a syringe.

86. The fluid testing assembly of illustrative embodiment 84, wherein the fluid collection device is a vacutainer.

87. The fluid testing assembly of illustrative embodiment 86, wherein the vacutainer includes a housing sealed with a stopper, and wherein the fluid testing device includes a needle positioned through the stopper.

88. A fluid testing assembly, comprising:
a fluid testing device, comprising:
a housing constructed of a fluid impermeable material;
a treatment window formed in the housing, the treatment window constructed of a material capable of passing forces into the housing; and
a transducer positioned adjacent to the treatment window, the transducer being configured to selectively generate forces directed through the treatment window of the housing and into a fluid sample to separate the fluid sample into a first constituent part and a second constituent part.

89. The fluid testing assembly of illustrative embodiment 88, wherein the transducer is an acoustic transducer.

90. The fluid testing assembly of illustrative embodiment 88, wherein the transducer is a magnetic transducer.

91. The fluid testing assembly of illustrative embodiment 88, wherein the transducer is a dielectrophoretic transducer.

92. The fluid testing assembly of any one of illustrative embodiments 88-91, wherein the housing defines a first channel and a second channel, adjacent to the treatment window such that the first channel is positioned to receive the first constituent part and the second channel is positioned to receive the second constituent part.

93. The fluid testing assembly of any one of illustrative embodiments 88-92, wherein the housing includes an optical zone formed in the treatment window of the housing, the optical zone constructed of a material that allows a colorimetric analysis of the fluid sample positioned within the housing, and located adjacent to the optical zone.

94. The fluid testing assembly of any one of illustrative embodiments 88-93, wherein the fluid testing device is integrated with a fluid collection device.

95. The fluid testing assembly of illustrative embodiment 94, wherein the fluid collection device is a syringe.

96. The fluid testing assembly of illustrative embodiment 94, wherein the fluid collection device is a vacutainer.

97. The fluid testing assembly of illustrative embodiment 96, wherein the vacutainer includes a housing sealed with a stopper, and wherein the fluid testing device includes a needle positioned through the stopper.

98. A blood testing assembly, comprising:
a blood testing device, comprising:
a housing constructed of a fluid impermeable material;
a treatment window formed in the housing, the treatment window constructed of a material capable of passing acoustic forces into the housing;
an optical zone formed in the treatment window of the housing, the optical zone constructed of a material that allows a colorimetric analysis of a blood sample positioned within the housing, and located adjacent to the optical zone; and
a reader, comprising:
an acoustic transducer position to selectively generate acoustic forces directed through the treatment window of the housing and into the blood sample; and
a control unit for selectively actuating and deactuating the acoustic transducer.

99. A method, comprising:
within a fluid treatment module, separating blood cells from plasma within a blood sample into a first zone containing plasma and blood cells, and a second zone containing plasma and being substantially devoid of blood cells; and
colorimetrically analyzing the plasma within the second zone to determine a degree of hemolysis within the blood sample.

100. The method of illustrative embodiment 99, wherein the fluid treatment module includes a housing constructed of a fluid impermeable material, and defining a first fluid port, and a second fluid port, the first fluid port configured to connect to a fluid collection device to receive a fluid sample from the fluid collection device into the housing, and the second port configured to pass the fluid sample from the housing into a testing instrument.

101. The method of illustrative embodiment 99, further comprising connecting a first fluid port of the fluid treatment module to a second fluid port of a syringe containing the blood sample; and passing a portion of the blood sample into the fluid treatment module.

102. A method, comprising:
within a blood testing device having a plunger positioned within a housing in which the plunger and an interior surface of the housing define a fluid reservoir, separating blood cells from plasma within a blood sample into a first zone containing plasma and blood cells, and a second zone containing plasma and being substantially devoid of blood cells; and
colorimetrically analyzing the plasma within the second zone to determine a degree of hemolysis within the blood sample.

103. A syringe, comprising:
a housing having a first fluid reservoir;
a plunger positioned within the housing and bordering the first fluid reservoir; and means for testing a fluid sample when the fluid sample is positioned within the housing.

From the above description, it is clear that the inventive concepts disclosed herein is well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the scope and coverage of the inventive concepts disclosed and claimed herein.

What is claimed is:
1. A device, comprising:
a housing constructed of a fluid impermeable material and defining a first fluid port and a second fluid port, the first fluid port configured to connect to a fluid collection device to form a fluid tight seal upon the first fluid port being connected to the fluid collection device, the first fluid port configured to receive a fluid sample from the fluid collection device into the housing, wherein the fluid sample is blood having red blood cells and plasma, and the second fluid port is configured to pass the fluid sample from the housing into an external testing instrument;
a zone formed in the housing, the zone constructed of a material that allows an analysis of the fluid sample positioned within the housing and located adjacent to the zone, the zone being an optical zone constructed of a material that is transparent to visible light; and
a lateral flow membrane configured to separate the red blood cells from the plasma to present plasma substantially devoid of red blood cells within the optical zone.

2. The device of claim 1, wherein the lateral flow membrane is supported by the housing and positioned adjacent to the zone such that the fluid sample passed from the first fluid port to the lateral flow membrane is treated prior to entering the zone.

3. The device of claim 1, wherein the housing is separate from the fluid collection device, and wherein the fluid collection device is a syringe.

4. The device of claim 1, wherein the fluid collection device is a syringe, and the testing instrument is an analyzer.

5. The device of claim 4, wherein the analyzer is a blood gas analyzer.

6. The device of claim 1, wherein the lateral flow membrane is devoid of treatment with a reagent.

7. The device of claim 1, wherein the housing has an upper portion, a lower portion and a side, and wherein the lateral flow membrane is situated on the side of the housing.

8. The device of claim 1, wherein the housing has an upper portion, a lower portion, and a longitudinal axis extending between the upper portion and the lower portion, and wherein the lateral flow membrane has a major axis extending in a nonparallel relationship with the longitudinal axis.

9. The device of claim 8, wherein the major axis extends side to side relative to the longitudinal axis.

10. The device of claim 1, wherein the housing defines a third fluid port positioned between the first fluid port and the second fluid port, and further comprising a gas permeable/liquid impermeable membrane covering the third fluid port.

11. The device of claim 2, wherein the lateral flow membrane is treated with a reagent.

12. The device of claim 2, wherein the lateral flow membrane has a distal end in the zone, and wherein the distal end is treated with a reagent.

13. The device of claim 2, wherein the lateral flow membrane has a proximal end away from the zone, and wherein the proximal end is treated with a reagent.

14. The device of claim 1, wherein the first fluid port includes a needle.

15. The device of claim 1, wherein the second fluid port is a luer connector.

16. The device of claim 1, wherein the second fluid port is a male port.

17. The device of claim 1, wherein the second fluid port is a female port.

* * * * *